(12) United States Patent
O'Connor et al.

(10) Patent No.: US 7,399,636 B2
(45) Date of Patent: Jul. 15, 2008

(54) DIAGNOSTIC KIT FOR PREDICTING PREGNANCY OUTCOME

(75) Inventors: John F. O'Connor, New Rochelle, NY (US); Galina I. Kovalevskaya, New York, NY (US); Steven Birken, Dumont, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 278 days.

(21) Appl. No.: 10/335,115

(22) Filed: Dec. 31, 2002

(65) Prior Publication Data

US 2003/0124737 A1   Jul. 3, 2003

Related U.S. Application Data

(63) Continuation of application No. 09/017,976, filed on Feb. 3, 1998, now Pat. No. 6,500,627.

(51) Int. Cl.
*G01N 33/48* (2006.01)
*G01N 33/53* (2006.01)
*C07K 16/00* (2006.01)

(52) U.S. Cl. .............. 436/65; 422/61; 435/7.1; 435/7.5; 435/7.92; 435/7.94; 436/501; 436/518; 436/524; 436/528; 436/65; 436/547; 436/548; 530/387.5; 530/388.24; 530/389.2

(58) Field of Classification Search ................ 435/7.1, 435/7.5, 7.92, 287.9, 7.94, 971; 436/501, 436/524, 528, 546, 166, 808, 814, 818, 518, 436/65, 547, 548, 811; 530/387.5, 388.24, 530/389.2; 422/61

See application file for complete search history.

(56) References Cited

U.S. PATENT DOCUMENTS

| 4,444,879 | A | * | 4/1984 | Foster et al. | ............... 435/7.95 |
| 4,514,505 | A | | 4/1985 | Canfield et al. | ............. 436/500 |
| 5,260,421 | A | | 11/1993 | Chappel et al. | ............. 530/397 |

(Continued)

FOREIGN PATENT DOCUMENTS

JP   4300896   10/1992

(Continued)

OTHER PUBLICATIONS

European Search Report (supplemental) dated Apr. 10, 2003.

(Continued)

*Primary Examiner*—Gailene R Gabel
(74) *Attorney, Agent, or Firm*—John P. White; Cooper & Dunham LLP

(57) ABSTRACT

The present invention provides a method of predicting pregnancy outcome in a subject by determining the amount of an early pregnancy associated molecular isoform of hCG in a sample. The present invention further provides a method for determining the amount of early pregnancy associated molecular isoforms of human chorionic gonadotropin (hCG) in a sample. The present invention also provides a diagnostic kit for determining the amount of early pregnancy associated hCG is a sample. The present invention additionally provides an antibody which specifically binds to an early pregnancy associated molecular isoform of human chorionic gonadotropin. Finally, the present invention provides methods for detecting trophoblast or non-trophoblast malignancy in a sample.

6 Claims, 12 Drawing Sheets

U.S. PATENT DOCUMENTS

| | | | | |
|---|---|---|---|---|
| 6,133,048 | A | 10/2000 | Penfold et al. | 436/533 |
| 6,339,143 | B1* | 1/2002 | Krichevsky et al. | 530/388.24 |
| 6,429,018 | B1* | 8/2002 | Cole et al. | 436/87 |
| 6,500,627 | B1* | 12/2002 | O'Connor et al. | 435/7.92 |
| 9,918,297 | | 1/2003 | Pandian et al. | 436/65 |

FOREIGN PATENT DOCUMENTS

| | | |
|---|---|---|
| WO | 8804779 | 6/1988 |
| WO | WO8804779 | 6/1988 |
| WO | 9941584 | 8/1999 |
| WO | WO0070094 | 12/2000 |

OTHER PUBLICATIONS

Huang, S. et al. (1988) "A chromatofocusing study of human chorionic gonadotropin in biological fluids in normal pregnancy, pre-eclampsia and choriocarcinoma," J. Formos Med. Assoc. 87:1036-44.

Kovalevskaya, G. et al. (2002) "Differential expression of human chorionic gonadotropin (hCG) glycosylation isoforms in failing and continuing pregnancies: preliminary characterization of the hyperglycosylated hCG epitope," J. Endocrinology 172:497-506.

European Search Report dated Nov. 20, 2002 (Exhibit 7).

PCT International Search Report dated Sep. 13, 1999 (Exhibit 8).

PCT International Search Report dated Aug. 11, 2000 (Exhibit 9).

European Search Report dated Mar. 20, 2003 (Exhibit 2).

Cole, L.A. (1998) "hCG, its free subunits and its metabolites. Roles in pregnancy and trophoblastic disease," J. Reprod. Med. 43(1):3-10 (Exhibit 3).

Ehrlich P.H. and Moyle W.R. (1983) "Cooperative immunoassays: ultrasensitive assays with mixed monoclonal antibodies," Science 221:279-81 (Exhibit 4).

Ehrlich P.H. et al. (1982) "Mixing two monoclonal antibodies yields enhanced affinity for antigen," J. Immunol. 128(6):2709-13 (Exhibit 5).

Ehrlich P.H. et al. (1985) "Characterization and relative orientation of epitopes for monoclonal antibodies and antisera to human chorionic gonadotropin," Am. J. Reprod. Immunol. Microbiol. 8(2):48-54 (Exhibit 6).

Ehrlich P.H. et al. (1985) "Monoclonal antibodies to gonadotropin subunits," Methods Enzymol. 109:638-55 (Exhibit 7).

Elliott, M.M. et al. (1997) "Carbohydrate and peptide structure of the alpha and beta-subunits of human chorionic gonadotropin from normal and aberrant pregnancy and choriocarcinoma," Endocrine 7(1):15-32 (Exhibit 8).

Kardana, A. et al. (1991) "The heterogeneity of human chorionic gonadotropin (hCG). I. Characterization of peptide heterogeneity in 13 individual preparations of hCG," Endocrinology 129(3):1541-50 (Exhibit 9).

Bogart, M.H., Pandiant, M.R. and Jones, O.W. (1987) "Abnormal maternal serum chorionic gonadotropin levels in pregnancies with fetal chromosome abnormalities," Prenat. Diagn. 7:623-630 (Exhibit 7).

Bogart, M., Golbust, M., Nancy, S. and Jones, W. (1989) "Human chorionic gonadotropin levels in pregnancies with aneuploid fetuses," Prenat. Diagn. 9:379-384 (Exhibit 8).

Cole, L.A., Cermik, D. and Bahado-Singh, R. (1997) "Oligosaccharide variants of hCG-related molecules: potential screening markers for Down syndrome," Prenat. Diagn. 17:1188-1190 (Exhibit 9).

Cole, L.A., Isozaki, T. and Jones, E. (1997) "Urine β-core fragment, a potential screening test for ectopic pregnancy and spontaneous abortion," Fetal. Diagn. Ther. 12:336-339 (Exhibit 10).

Cole, L., Omrani, A., Cermik, D., Bahado-Singh, R. and Mahoney, M. (1998) "Hyperglycosylated hCG, a potential alternative to hCG in Down syndrome screening," Prenat. Diagn. 18:926-933 (Exhibit 11).

Forest, J. Masse, J., Rousseau, F., Moutquin, J., Brideau, N. and Belanger, M. (1995) "Screening for Down syndrome during the first and second trimesters: impact of risk estimation parameters," Clin. Biochem. 28: 443-449 (Exhibit 12).

Kovalevskaya, G., Birken, S., Kakuma, T. and O'Connor, J.F. (1999) "Early pregnancy human chorionic gonadotropin (hCG) isoforms measured by an immunometric assay for choriocarcinoma-like hCG," J. Endocrinol. 161: 99-106 (Exhibit 13).

Spencer, K., Macri, J.N., Carpenter, P., Anderson, R. and Krantz, D. (1993) "Stability of intact chorionic gonadotropin (hCG) in serum, liquid whole blood, and dried whole-blood filter-paper spots: impact on screening for Down syndrome by measurement of free β-hCG subunit," Clin. Chem. 39:1064-1068 (Exhibit 14).

Spencer, K., Aitken, D.A., Macri, J.N. and Buchanan, P.D. (1996) "Urine free beta-hCG and beta core in pregnancies affected by Down's syndrome," Prenat. Diagn. 16:605-613 (Exhibit 15).

Spencer, K., Muller, F. and Aitken, D.A. (1997) "Biochemical markers of trisomy 21 in amniotic fluid," Prenat. Diagn. 17:31-37 (Exhibit 16).

Valerio, D., Aiello, R., Altieri, V. and Fagnoni, P. (1996) "Maternal serum screening of fetal chromosomal abnormalities by AFP, UE3, hCG and free-βhCG," Minerva. Ginecol. 48:169-173 (Exhibit 17).

Wald, N.J., Densem, W., Smith, D. and Klee, G.G. (1994) "Four-marker serum screening for Down's syndrome," Prenat. Diagn. 14:707-716 (Exhibit 18).

Wald, N.J., Kennard, A. and Smith, D. (1994) "First trimester biochemical screening for Down's syndrome," Ann. Med. 26:23-29 (Exhibit 19).

Zimmermann, R., Reynolds, T.M., John, R., Spencer, K., Bartels, I., Coombes, E. and Trevor, S. (1996) "Age-independent indices in second-trimester serum screening for Down's syndrome are useless," Prenat. Diagn. 16:79-82 (Exhibit 20).

Acevedo, H.F., Krichvesky, A., Campbell-Acevedo, E.A., Galyon, J.C., Buffo, M.J. and Hartsock, R.J. (1992) "Expression of membrane-associated human chorionic gonadotropin, its subunits, and fragments by cultured human cancer cells," Cancer 69(7) :1829-1842.

Berger, P., Schwarz, S., Spottl, G., Wick, G. and Mann, K. (1993) "Variants of human chorionic gonadotropin from pregnant women and tumor patients recognized by monoclonal antibodies," J. Clin. Endocrinol. Metab. 77(2):247-351.

Birken, S., Chen, Y., Gawinowicz, M.A., Lustbader, J.W., Pollak, S., Agosto, G., Buck, R. and O'Connor, J. (1993) "Separation of nicked human chorionic gonadotropin (hCG), intact hCG, and hCG beta fragment from standard reference preparations and raw urine samples," Endocrinology, 133:1390-1397.

Birken, S., Kovalevskaya, G. and O'Connor, J. (1996) "Metabolism of hCG and hLH to multiple urinary forms," Mol. Cell. Endocrinol. 125:121-131.

Birken, S., Maydelman, Y., Gawinowicz, M.A., Pound, A., Liu, Y. and Hartree, A.S. (1996) "Isolation and characterization of human pituitary chorionic gonadotropin," Endocrinology 137:1402-1411.

Birken, S., Krichevsky, A., O'Connor, J., Schlatterer, J., Cole, L., Kardana, A. and Canfield, R. (1999) "Development and characterization of antibodies to a nicked and hyperglycosylated form of hCG from a choriocarcinoma patient," Endocrinology 10(2):137-144.

Cole, L.A., Birken, S. and Perini, F. (1985) "The structures of the serine-linked sugar chains on human chorionic gonadotropin," Biochem. Biophys. Res. Commun. 126:333-339.

Cole, L., Kardana, A., Andrade-Gordon, P., Gawinowicz, M., Morris, J., Bergert, E., O'Connor, J. and Birken, S. (1991) "The heterogeneity of human chorionic gonadotropin (hCG). III. The occurence and biological and immunological activities of nicked hCG," Endocrinology 129 (3):1559-1567.

Cole, L.A., Kardana, A., Park, S.Y. and Braunstein, G.D. (1993) "The deactivation of hCG by nicking and dissociation," J. Clin. Endocrinol. Metab. 76:704-710.

Ellish, N.J., Saboda, K., O'Connor, J., Nasca, P.C., Stanek, E.F., Boyle, C. (1996) "A prospective study of early pregnancy loss," Hum. Reprod. 11:406-412

Hoermann, R., Spoettl, G., Grossmann, M., Saller, B. and Mann, K. (1993) "Molecular heterogeneity of human chorionic gonadotropin in serum and urine from patients with trophoblastic tumors," Clin. Invest. 71:953-960.

Hoermann, R., Berger, P., Spoettl, G., Gillesberger, F., Kardana, A., Cole, L.A. and Mann, K. (1994) "Immunological recognition and clinical significance of nicked human chroionic gonadotropin in testicular cancer," *Clin. Chem.* 40:2306-2312.

Knight, P. (1989) "The carbohydrate frontier," *Bio/Techniques* 7(1):35-36, 39-40.

Kovalevskaya, G., Birken, S., O'Connor, J.F., Schlatterer, J., Maydelman, Y. and Canfield, R. (1995) "hLH beta core fragment immunoreactivity in the urine of ovulating women: a sensitive and specific immunometric assay for its detection," *Endocrine* 3:881-887.

Kovalevskaya, G., Birken, S., Kakuma, T., Schlatterer, J. and O'Connor, J. (1999) "Evaluation of nicked human chorionic gonadotropin content in clinical specimens by a specific immunometric assay," *Clin. Chem.* 45(1):68-77.

O'Connor, J.F., Ellish, N., Kakuma, T., Schlatterer, H. and Kovalevsakaya, G. (1998) "Differential urinary gonadotrophin profiles in early pregnancy and early pregnancy loss," *Prenat. Diagn.* 18:1-9.

Wilcox, A.J., Weinberg, C.R., O'Connor, J.F., Baird, D.D., Schlatterer, J.P., Canfield, R.E., Armstrong, E.G. and Nisula, B.C. (1988) "Incidence of early loss of pregnancy," *N. Engl. J. Med.* 319:189-194.

O'Connor, J.F., Schlatterer, J.P., Birken, S., Krichevsky, A., Armstrong, E.G., McMahon, D. and Canfield, R.E. (1988) "Development of highly sensitive immunoassays to measure human chorionic gonadotropin, its beta-subunit, and beta core fragment in the urine: application to malignancies," *Cancer Res.* 48:1361-1366.

O'Connor, J.F., Birken, S., Lustbader, J.W., Krichevsky, A., Chen, Y. and Canfield, R.E. (1994) "Recent advances in the chemistry and immunochemistry of human chorionic gonadotropin: impact on clinical measurements," [Review] *Endocr. Rev.* 15:650-683.

O'Connor, J.F., Ellish, N., Kakuma, T., Schlatterer, H. and Kovalevsakaya, G. (1998) "Differential urinary gonadotrophin profiles in early pregnancy and early pregnancy loss," *Prenat. Diagn.* 18:1-9.

Wilcox, A.J., Weinberg, C.R., O'Connor, J. F., Baird, D.D., Schlatterer, J.P., Canfield, R.E., Armstrong, E.G. and Nisula, B.C. (1998) "Incidence of early loss of pregnancy," *N. Engl. J. Med.* 319:189-194.

Zinaman, M.J., Clegg, E.D., Brown, C.C., O'Connor, J. and Selevan, S.G. (1996) "Estimates of human fertility and pregnancy loss," *Fertil. Steril.* 65:503-509.

\* cited by examiner

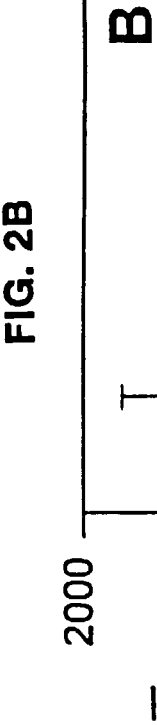
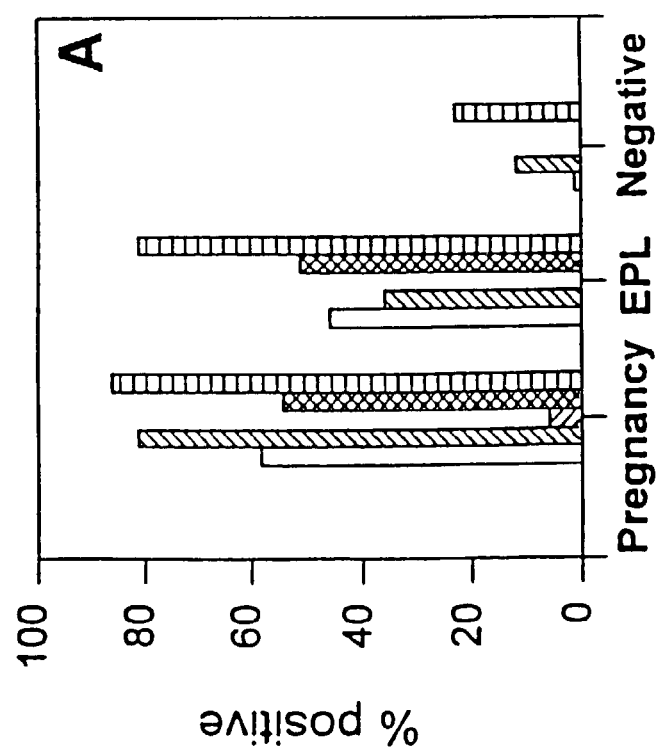
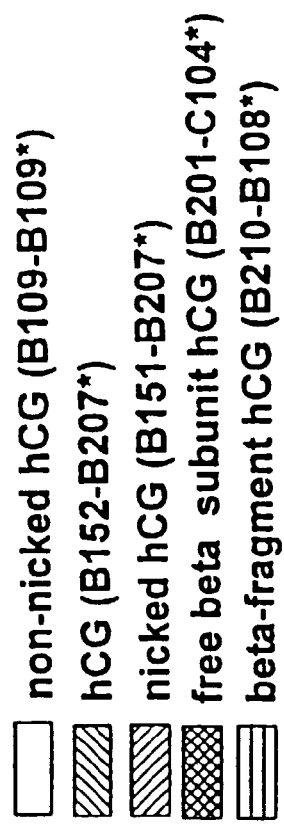
FIG. 2A
FIG. 2B

● hCG   ■ nhCG   ▲ hCGβ   ▼ nhCGβ   ♦ hCGβcf

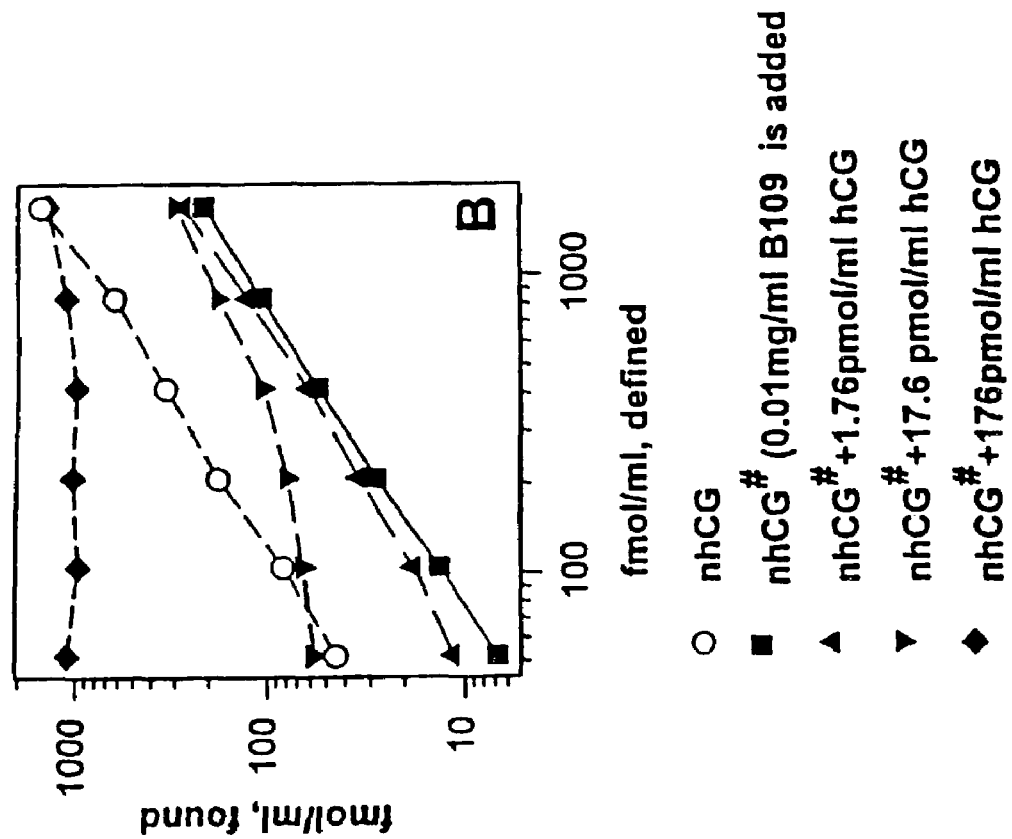
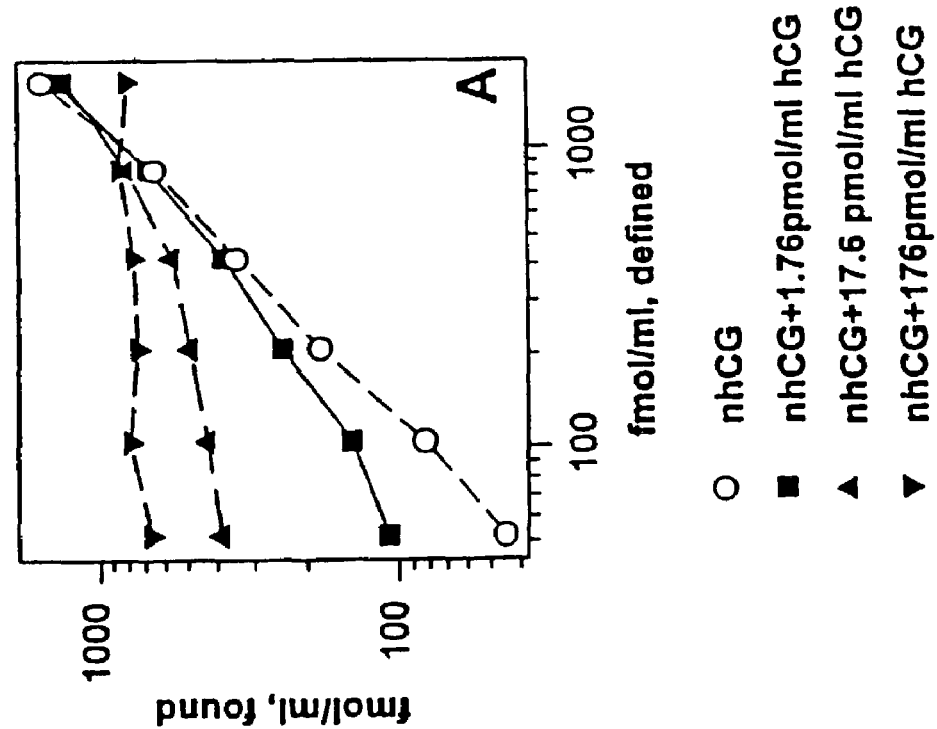
FIG. 4A
FIG. 4B

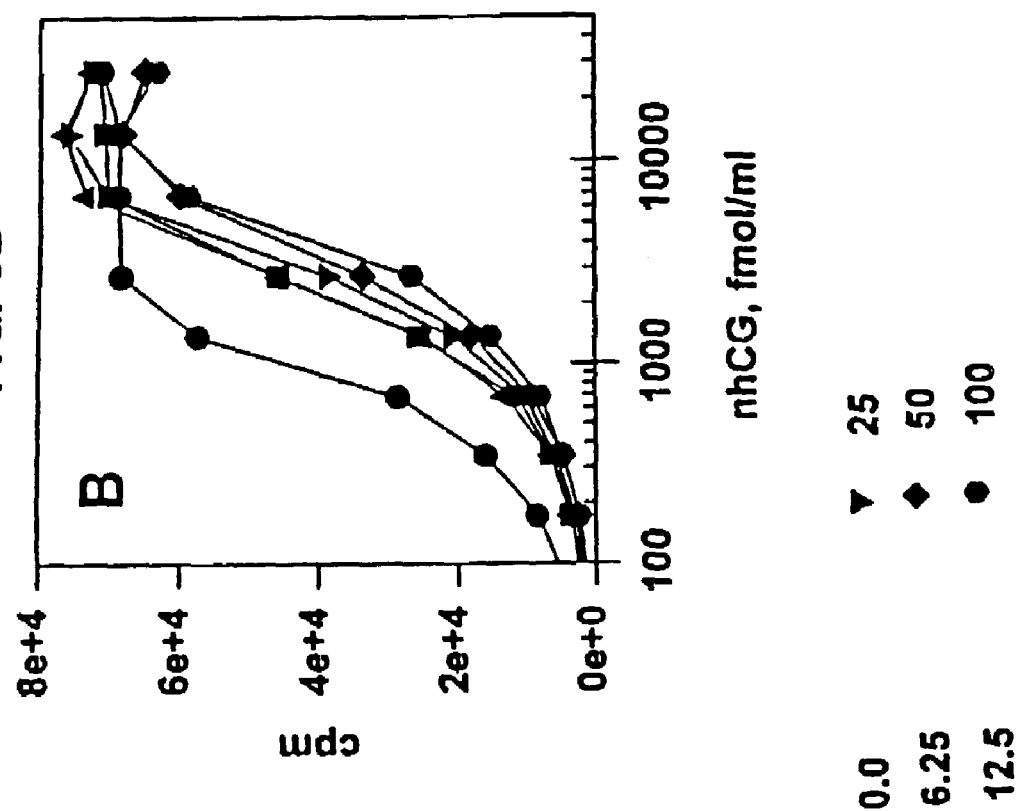
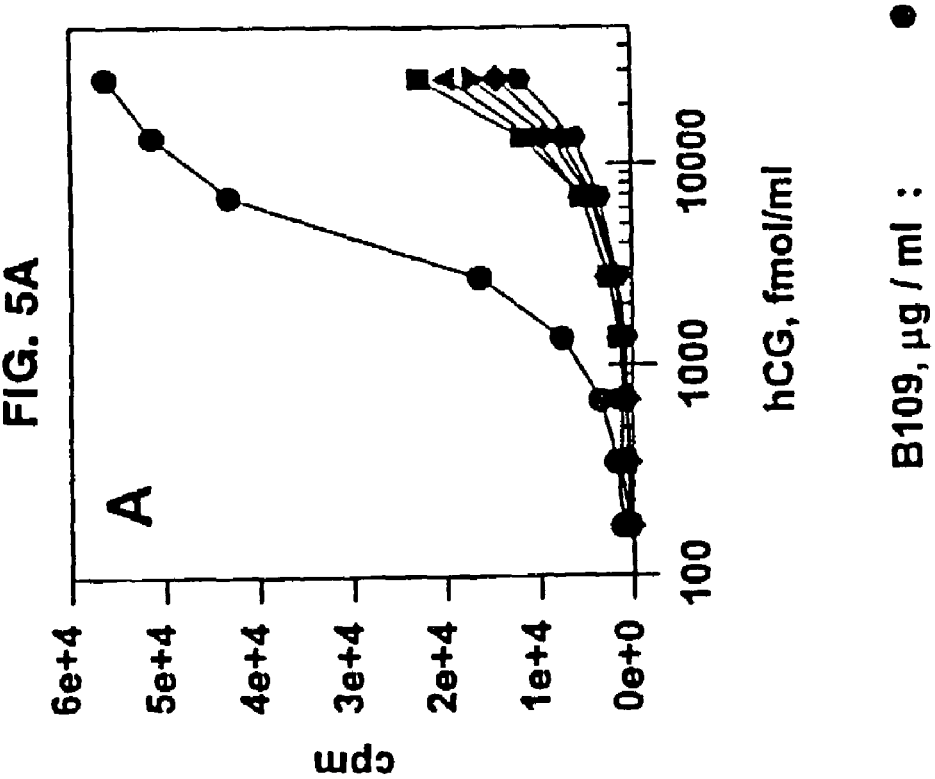

- B109-B108*
- B151-B207*
- ▲ B152-B207*
- ▼ B201-C104*
- ◆ B210-B108*

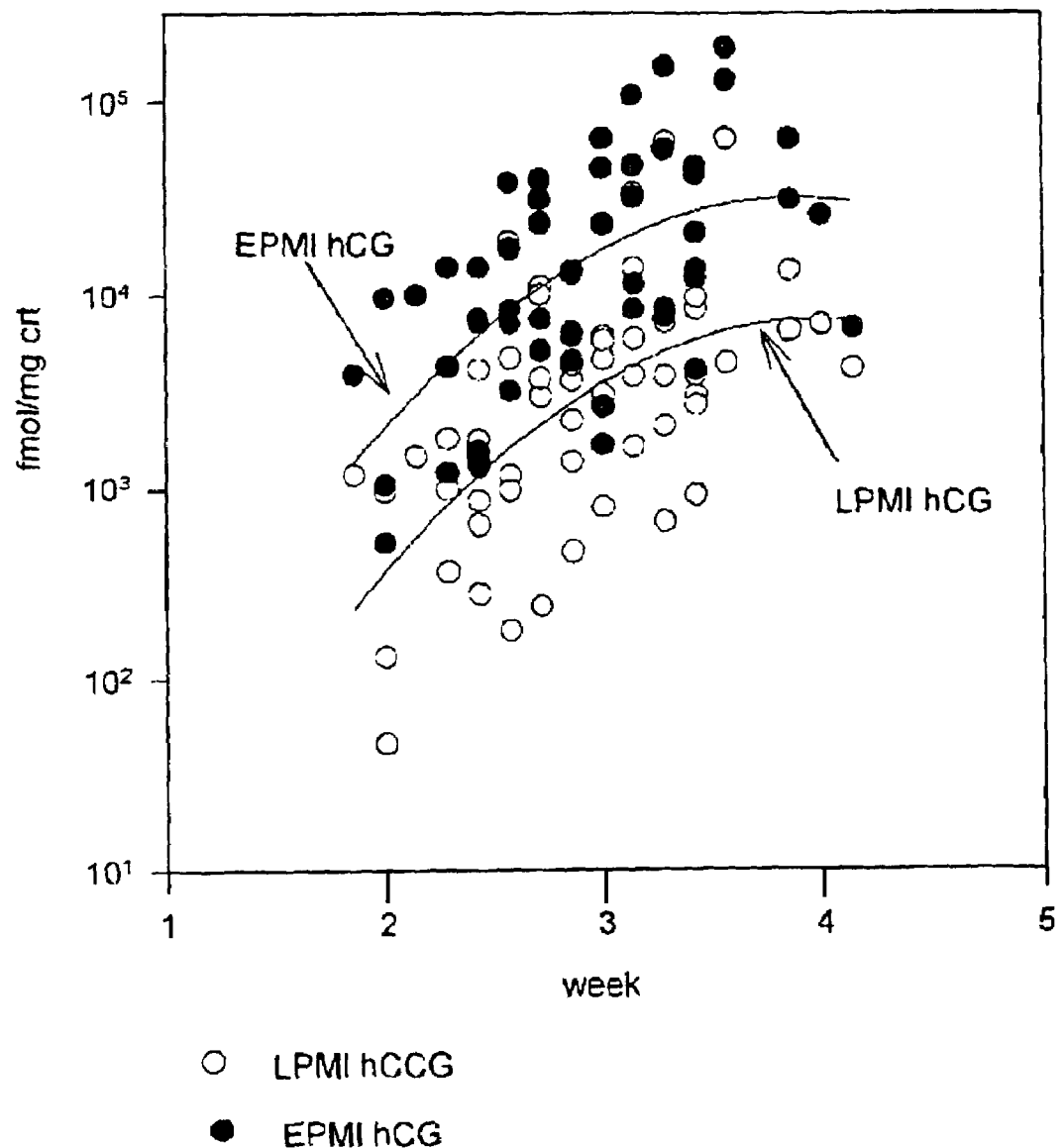

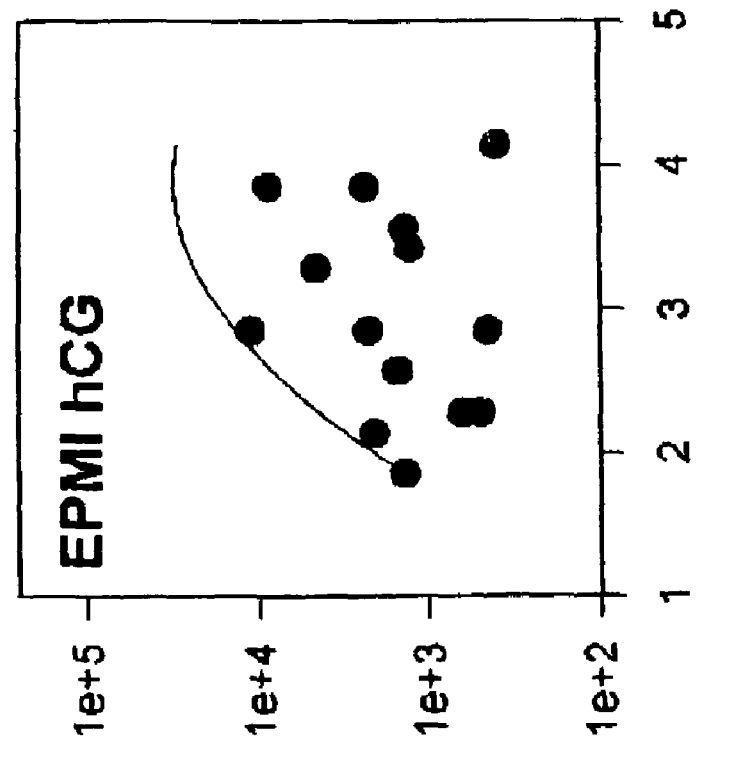
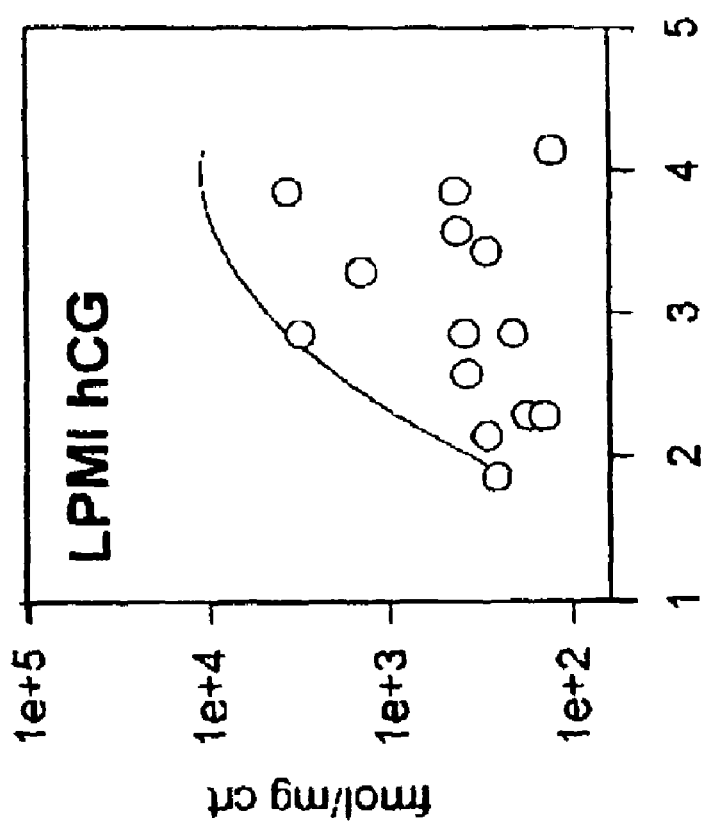
FIG. 10A
FIG. 10B

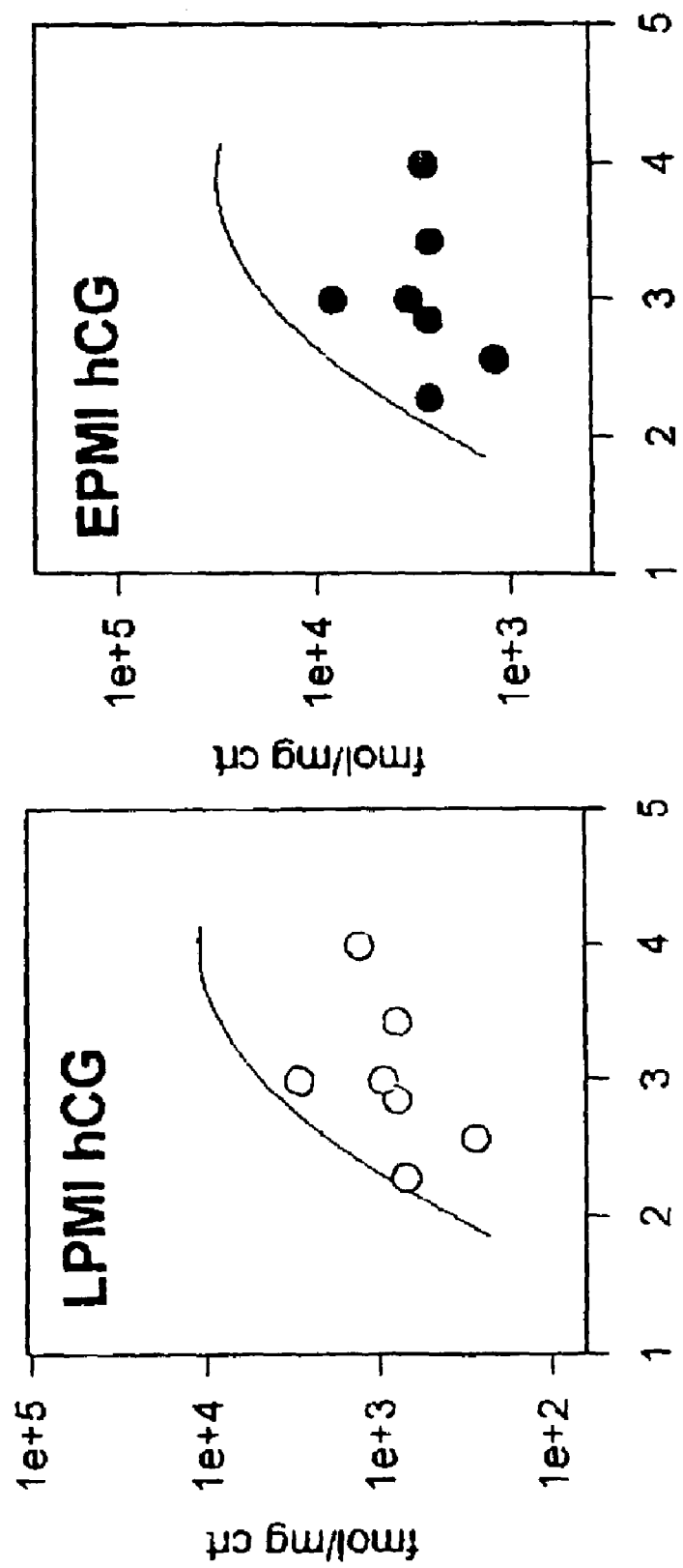

DIAGNOSTIC KIT FOR PREDICTING PREGNANCY OUTCOME

This application is a continuation of U.S. Ser. No. 09/017,976, filed Feb. 3, 1998 now U.S. Pat. No. 6,500,627, the content of which is hereby incorporated into this application by reference.

The invention disclosed herein was made with United States Government support under National Institutes of Health Grant Nos. NIEHS ES-07589 and HD 15454. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art.

Early pregnancy loss (EPL) is a widespread, but largely undiagnosed problem. In order to adequately diagnose and develop treatments for EPL it is essential to be able to measure the rate of occurance of EPL. This is critically important in epidemiological studies, some of which are related to exposures to known or suspected reproductive toxins in the workplace, in the environment or by personal use. These early pregnancy losses are often not recognized by women or physicians and are detected solely by the measurement of hCG in the urine at the time between implantation and expected menses. They are sometimes termed "chemical pregnancies" or "occult pregnancies." A landmark epidemiological study established that the incidence of EPL was 22% in a population of healthy women attempting to conceive (Wilcox, A. J., et al., 1988). This investigation employed a very sensitive (0.01 ng/ml hCG) assay which detected only the intact hCG molecule with the unique beta subunit carboxyterminal peptide present.

There are multiple likely causes for EPL and clinical spontaneous abortion including genetic abnormality, immunological dysfunction, untreated infection or other unknown physiological problems. In addition, losses may be caused by failure of human chorionic gonadotropin (hCG) to induce adequate response at its target, the corpus luteum. This could result from inadequate hormonal potency. "Nicking" of the beta subunit in the loop 2 region of the molecule, specifically between residues 44-49, can reduce biopotency of hCG. Cleaved peptide bonds in this area of the molecule also exhibit reduced biopotency and reduced immunochemical recognition by monoclonal antibodies directed to the heterodimeric hormone (Cole, L. A., et al., 1991a; Cole, L. A., et al., 1991b; Puisieux, A., et al., 1990; Nishimura, R., et al., 1988; Nishimura, R. T., et al., 1989). Nicked forms of hCG were examined as possibly more prevalent in EPL situations and, at least in part, responsible for early pregnancy loss. Unfortunately, many of the reports claiming that substantial concentrations of nicked hCG are produced during pregnancy losses or successful pregnancies, are not accurate due to faulty assumptions regarding assay specificity (Wilcox, A. J., et al., 1988). Carbohydrate-modified hCG can also exhibit reduced biopotency due to increased clearance by the liver. For example, if the hCG has significantly reduced sialic acid content and carbohydrate chains terminating in galactose, much hCG will be removed by a liver receptor for such altered glycoproteins (Braun, J. K., et al., 1996; Kawasaki, T. and G. Ashwell, 1996). Thus, the circulating life-time of asialo hCG is reduced and its in vivo potency is low. Other carbohydrate changes also alter circulating half life. For example, glycoproteins terminating in sulfate-N-acetyl galactosamine are also extracted by a specific liver receptor and have a reduced circulating lifetime (Baenziger, J. U., 1994; Fiete, D., et al., 1991).

At least two factors affect increased potency of hCG. First, it is known that a larger Stoke's radius will decrease clearance through the kidney glomerulus which generally clears proteins above an effective size of 70,000 very slowly. The effective size of urinary-isolated hCG is just at this borderline reduced clearance size. Generally, extra sugar content makes the hydrated radius of glycoproteins larger. It has been shown that by adding the hCG beta COOH-terminal peptide to hFSH or hLH, their circulating life-times greatly increased (Fares, F. A. et al., 1992; Matzuk, M. M., 1990). This addition was thought mostly due to the carbohydrate content of that peptide rather than simply the extra polypeptide size (Wilcox, A. J., et al., 1988). Second, increased negative charge of a protein will prolong its circulating time because of decreased renal clearance (Chmielewski, C. 1992, Quadri, K. H., et al., 1994; Maack, T., et al., 1985). This increased negative charge can be due to extra sialic acid or other negative groups, including sulfate such as is present on hLH and on the pituitary form of hCG (Birken, S., et al., 1996b). Changes which affect signal transduction at the receptor may also affect biopotency of hCG. It is known that deglycosylated hCG has much reduced receptor potency (Ravindranath, N., et al., 1992; Sairam, M. R., and L. G., Jiang, 1992; Browne, E. S., et al., 1990; Sairam, M. R., 1989; Sairam, M. R., et al., 1988). Carbohydrate reduced forms of hCG also have reduced signal transduction (Amano, J., et al., 1990; Bahl, O. P., et al., 1995; Moyle, W. R., 1975).

According to the present invention EPL or recurrent spontaneous abortion is not due to an abnormal hCG form that has reduced potency, such as nicked hCG. Instead, the present invention provides evidence that in successful outcome pregnancies women usually produce forms of hCG which are very highly potent in very early pregnancy; the standard urinary reference preparations of hCG are less potent forms of the hormone produced later in pregnancy. The increased potency could be caused by a combination of factors from circulating half-life to increased receptor affinity or signal transduction or all of the preceding. Since hCG is low very early in pregnancy, it is logical to find a more potent form of hCG on a molar basis to carry out its function until production levels rise as the trophoblastic cellular mass increases. The present invention describes molecular and immunological tools and methods including an antibody, B152, described herein which recognizes the highly potent early pregnancy associated molecular isoforms of hCG.

The determination of blood and urine profiles for the B152 hCG isoforms throughout healthy pregnancies can delineate the pattern of isoforms in successful pregnancies. These isoforms can be measured by immunoassay alone, obviating the need to perform complex isoelectric focusing studies or other separation techniques. Additionally, the methods decribed herein are applicable to large numbers of samples.

SUMMARY OF THE INVENTION

The present invention provides a method of predicting pregnancy outcome in a subject by determining the amount of an early pregnancy associated molecular isoform of hCG in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) measuring the amount of complexes formed, thereby determining the amount of the early pregnancy associated molecular isoform of hCG in the sample; and (c) comparing the amount early pregnancy associated molecular isoform of hCG in the sample determined in step (b) with either (i) the amount determined for temporally matched, normal pregnant subject(s) or (ii) the amount determined for non-pregnant subject(s), wherein the relative absence of the early pregnancy associated molecular isoform of hCG in the sample indicates a negative outcome of pregnancy for the subject.

The present invention further provides a method of predicting pregnancy outcome in a subject by determining the amount of an early pregnancy associated molecular isoform of hCG in a sample comprising: (a) contacting a capturing antibody which specifically binds to the early pregnancy associated molecular isoform of hCG with a solid matrix under conditions permitting binding of the antibody with the solid matrix; (b) contacting the bound matrix with the sample under conditions permitting binding of the antigen present in the sample with the capturing antibody; (c) separating the bound matrix and the sample; (d) contacting the separated bound matrix with a detecting antibody which specifically binds to hCG under conditions permitting binding of antibody and antigen in the sample; (e) measuring the amount of bound antibody on the bound matrix, thereby determining the amount of early pregnancy associated molecular isoform of hCG in the sample;

and (f) comparing the amount early pregnancy associated molecular isoform of hCG in the sample determined in step (e) with either (i) the amount determined for temporally matched, normal pregnant subject(s) or (ii) the amount determined for non-pregnant subject(s), wherein amounts of the early pregnancy associated molecular isoform of hCG in the sample similar to amounts of early pregnancy associated molecular isoform of hCG in temporally matched pregnant samples indicates a positive outcome, amounts of early pregnancy associated molecular isoform of hCG in the sample similar to amounts of early pregnancy associated molecular isoform of hCG in the non-pregnant samples indicates a negative outcome of pregnancy for the subject.

In addition, the present invention provides a method for determining the amount of early pregnancy associated molecular isoforms of in a sample comprising: (a) contacting the sample with an antibody which specifically binds to an early pregnancy associated molecular isoform of hCG under conditions permitting formation of a complex between the antibody and the early pregnancy associated molecular isoform of hCG; and (b) determining the amount of complexes formed thereby determining the amount of early pregnancy associated molecular isoform of hCG in the sample.

Further, the present invention provides a diagnostic kit for determining the amount of early pregnancy associated hCG is a sample comprising: (a) an antibody which specifically binds to an early pregnancy associated molecular isoform; (b) a solid matrix to which the antibody is bound; and (c) reagents permitting the formation of a complex between the antibody and a sample.

The present invention additionally provides an antibody which specifically binds to an early pregnancy associated molecular isoform of human chorionic gonadotropin.

Further, the present invention provides a method for detecting non-trophoblast malignancy in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample; and (d) comparing the amount of early pregnancy associated molecular isoform of hCG in the sample determined in step (b) with the amount of early pregnancy associated molecular isoform of hCG in the sample determined in step (c), wherein a positive detection of early pregnancy associated molecular isoform detected in step (b) and a relative absence of the early pregnancy associated molecular isoform of hCG detected in step (c) indicates the presence of non-trophoblast malignancy in the sample.

Finally, the present invention provides a method for detecting gestational trophoblast disease in a sample from a subject comprising (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample due to binding with the first antibody, and late pregnancy associated molecular isoform of hCG in the sample due to binding with the second antibody; (d) determining the ratio of early pregnancy associated molecular isoform of hCG to late pregnancy associated molecular isoform of hCG in the subject; and (e) comparing the ratio of early pregnancy associated molecular isoform of hCG to late pregnancy associated molecular isoform of hCG in the sample determined in step (c) over time, wherein a continuing high ratio of early pregnancy associated molecular isoform of hCG to late pregnancy associated molecular isoform of hCG in the sample determined in step (c) indicates the presence of gestational trophoblast disease in the subject.

Bioassay for forms of hCG. This is data from recombinant CHO cells expressing the LH/CG receptor. The response factor is cAMP production. The x-axis is dose of one of four callibrated, pure hormones as described on graph legends. Expressed hCG has no nicks; choriocarcinoma hCG (C5) is 100% nicked; CR 127 was purified into a nick-free (non-nicked, intact) and nick-enriched fraction as shown.

FIGS. 2A-2B

The percentage of positive samples (FIG. 2A) in the study for each of the analytes measured (In early normal pregnancy, EPL cycles and control, i.e. non-conceptive cycles. It is apparent that all of the characterized hCG urinary analytes, except nicked hCG, are expressed in both pregnancy and EPL. In the non-conceptive (control) cycles hCG beta core fragment is expressed at low levels in about 20% of the cycles FIG. 2B provides the levels of hCG analytes expression in the three types of cycles denominated above. Clearly, the pregnancy cycles produced greater amounts of analytes that did the loss cycles, with the most obvious difference being provided by the B152-B207* hCG assay. (Specimens were collected at days 9, 10, 11 post calculated day of ovulation.

FIGS. 3A-3H

Specificity characteristics of monoclonal antibodies to nicked hCG in liquid phase competitive assays.

FIGS. 4A-4B

Recovery nhCG in B151-B604* assay in the presence of increasing concentrations of hCG (FIG. 4A) and in the presence of B109 (0.01 mg/ml) as a scavenger for hCG (FIG. 4B).

FIGS. 5A-5B

Effect of different concentrations of B109 as a scavenger for hCG in B115-B108* assay (FIG. 5A) and effect of B109 in different concentrations on nicked hCG binding in B151-B108* assay (FIG. 5B).

FIG. 6

Ratio of hCG isoforms measured by the B152-B207* (early pregnancy associated molecular isoform (EPMI) hCG) and B109-B108* (late pregnancy associated molecular isoform (LPMI) hCG) assays in normal pregnancy urine (n=159) as a function of gestational age. (The second order regression curve and 95% confidence intervals are shown).

FIG. 7

Box plot of B152/B109 ratio (EPML/LPMI hCG) for pregnancy matched serum/urine specimens at 5-6 weeks of gestational age (n=5) and in JAR cell supernatant. Box extends to the 25th and 75th percentile. The upper and lower symbols indicate the 90th and 10th percentile respectively. A solid line inside the box marks the value of the 50th percentile. The ratio in JAR supernatant, choriocarcinoma cell line, is similar that in early pregnancy, i.e. B152-B207* may be more sensitive marker for the type of hCG produced in malignancy.

FIGS. 8A-8B

Figure 8A:
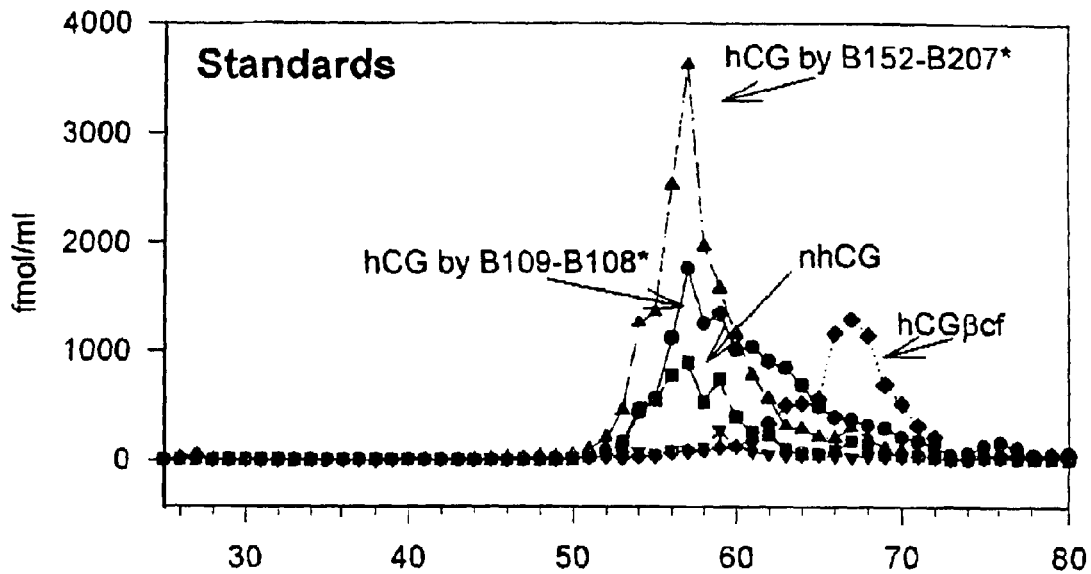

FIG. 8A. Dual tandem Superose 12 columns of standard preparation of intact hCG, nicked hCG and hCG beta core fragment as assessed by specific immunoassays.

Figure 8B:
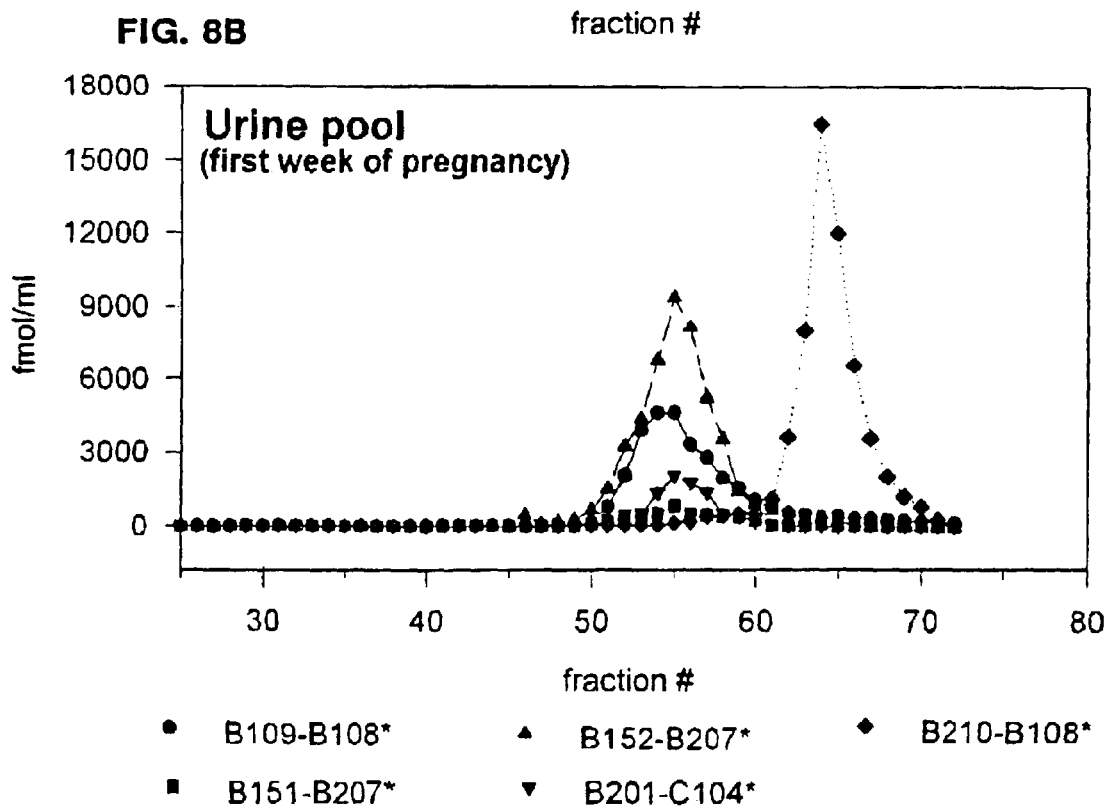

FIG. 8B. Dual tandem Superose 12 columns of a pooled early pregnancy urine concentrate (first week of gestation), illustrating that there is no additional signal for molecules of lower molecular size.

FIG. 9

Urinary concentration of EPMI hCG and LPMI hCG in the first 4 weeks of gestation (n=57). (The second order regression curve and molar concentrations values are shown).

FIGS. 10A-10D

Urinary concentration of EPMI and LPMI hCG in spontaneous abortion (n=14) and ectopic pregnancy (n=7) against matched gestational age normal pregnancy samples (n=57) (for normal pregnancy only regression curves shown). There is a statistically significant concentration difference between normal and ectopic pregnancy or spontaneous abortion both EPMI and LPMI. They both discriminate well on the basis of concentration.

FIG. 11

The urinary intact hCG profile expressed in fmol/mg creatinine throughout the pregnancy as measured by B109-B108* assay (LPMI hCG) and by B152-B207* assay (EPMI hCG) (n=159). EPMI appears earlier in gestation and decreases more substantially than does LPMI as pregnancy progresses.

DETAILED DESCRIPTION OF THE INVENTION

A method of predicting pregnancy outcome in a subject by determining the amount of an early pregnancy associated molecular isoform of hCG in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) measuring the amount of complexes formed, thereby determining the amount of the early pregnancy associated molecular isoform of hCG in the sample; and (c) comparing the amount early pregnancy associated molecular isoform of hCG in the sample determined in step (b) with either (i) the amount determined for temporally matched, normal pregnant subject(s) or (ii) the amount determined for non-pregnant subject(s), wherein the relative absence of the early pregnancy associated molecular isoform of hCG in the sample indicates a negative outcome of pregnancy for the subject. In an embodiment of the present invention, the antibody is B152. Another embodiment of this invention is the early pregnancy associated molecular isoform of hCG.

According to one embodiment of this invention, step (a) further comprises a second antibody which specifically binds to hCG without substantially cross-reacting with said antibody under conditions permitting formation of a complex between the antibody and the early pregnancy associated molecular isoform of hCG. In an embodiment of this invention, the second antibody is B207. According to another embodiment of this invention, step (a) further comprises a second antibody which specifically binds to intact non-nicked hCG without substantially cross-reacting with said antibody under conditions permitting formation of a complex between the antibody and the early pregnancy associated molecular isoform of hCG. In an embodiment of this invention, the second antibody is B108 or B109. In an embodiment of this invention, step (c) comprises comparing the amount of the early pregnancy associated molecular isoform of hCG determined in step (b) for said antibody with the amount determined in step (b) for the second antibody, wherein a high ratio of amounts determined for said antibody relative to the second antibody indicates a positive outcome of pregnancy for the subject, a low ratio indicates a negative outcome of pregnancy for the subject.

In yet another embodiment of this invention, step (c) comprises comparing the amount early pregnancy associated molecular isoform of hCG in the sample determined in step (b) with either (i) the amount determined for temporally matched, normal pregnant subject(s) or (ii) the amount determined for non-pregnant subject(s), wherein amounts of the early pregnancy associated molecular isoform of hCG in the sample similar to amounts of early pregnancy associated molecular isoform of hCG in temporally matched pregnant samples indicates a positive outcome, amounts of early pregnancy associated molecular isoform of hCG in the sample similar to amounts of early pregnancy associated molecular isoform of hCG in the non-pregnant samples indicates a negative outcome of pregnancy for the subject.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

The present invention further provides a method of predicting pregnancy outcome in a subject by determining the amount of an early pregnancy associated molecular isoform of hCG in a sample comprising: (a) contacting a capturing antibody which specifically binds to the early pregnancy associated molecular isoform of hCG with a solid matrix under conditions permitting binding of the antibody with the solid matrix; (b) contacting the bound matrix with the sample under conditions permitting binding of the antigen present in the sample with the capturing antibody; (c) separating the bound matrix and the sample; (d) contacting the separated bound matrix with a detecting antibody which specifically binds to hCG under conditions permitting binding of antibody and antigen in the sample; (e) measuring the amount of bound antibody on the bound matrix, thereby determining the amount of early pregnancy associated molecular isoform of hCG in the sample; and (f) comparing the amount early pregnancy associated molecular isoform of hCG in the sample determined in step (e) with either (i) the amount determined for temporally matched, normal pregnant subject(s) or (ii) the amount determined for non-pregnant subject(s), wherein amounts of the early pregnancy associated molecular isoform of hCG in the sample similar to amounts of early pregnancy associated molecular isoform of hCG in temporally matched pregnant samples indicates a positive outcome, amounts of early pregnancy associated molecular isoform of hCG in the sample similar to amounts of early pregnancy associated molecular isoform of hCG in the non-pregnant samples indicates a negative outcome of pregnancy for the subject.

An embodiment of this invention further comprises (a) removing of the sample from the matrix; and (b) washing the bound matrix with an appropriate buffer. In one embodiment of this invention, the capturing antibody is B152. In one embodiment of this invention, the detecting antibody is B207. In an embodiment of this invention, step (a) further comprises a second capturing antibody which specifically binds to intact non-nicked hCG without substantially cross-reacting with said antibody under conditions permitting formation of a complex between the antibody and the early pregnancy associated molecular isoform of hCG. According to an embodiment of this invention, the second capturing antibody is B108 or B109. In an embodiment of this invention, step (d) further comprises a second detecting antibody which specifically binds to hCG without substantially cross-reacting with said antibody under conditions permitting formation of a complex between the antibody and the early pregnancy associated molecular isoform of hCG. In an-embodiment of this invention, step (f) comprises comparing the amount of the early pregnancy associated molecular isoform of hCG determined in step (e) for said antibody with the amount determined in step (b) for the second antibody, wherein a high ratio of amounts determined for said antibody relative to the second antibody indicates a positive outcome of pregnancy for the subject, a low ratio indicates a negative outcome of pregnancy for the subject.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

In addition, the present invention provides a method for determining the amount of early pregnancy associated molecular isoforms of in a sample comprising: (a) contacting the sample with an antibody which specifically binds to an early pregnancy associated molecular isoform of hCG under conditions permitting formation of a complex between the antibody and the early pregnancy associated molecular isoform of hCG; and (b) determining the amount of complexes formed thereby determining the amount of early pregnancy associated molecular isoform of hCG in the sample.

According to an embodiment of this invention, the antibody specifically binds a region of the early pregnancy associated molecular isoform of hCG comprising a carbohydrate moiety. In one embodiment of this invention the antibody is produced by a hybridoma cell line. In one embodiment of this invention the antibody is B152.

Further, the present invention provides a diagnostic kit for determining the amount of early pregnancy associated hCG is a sample comprising: (a) an antibody which specifically binds to an early pregnancy associated molecular isoform; (b) a solid matrix to which the antibody is bound; and (c) reagents permitting the formation of a complex between the antibody and a sample. In an embodiment of this invention, the antibody is B108, B109 or B152. An embodiment of this invention further comprises control sample(s) normal pregnant sample(s), nonpregnant sample(s), or male sample(s).

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

The present invention additionally provides an antibody which specifically binds to an early pregnancy associated molecular isoform of human chorionic gonadotropin.

In an embodiment of this invention, the antibody specifically binds to a region of the early pregnancy associated molecular isoform of human chorionic gonadotropin comprising a carbohydrate moiety. According to one embodiment of this invention, the monoclonal antibody is B152. In an embodiment of this invention, a hybridoma cell (ATCC Accession No. HB-12467) is provided capable of producing monoclonal antibody B152. Another embodiment of this invention is the early pregnancy associated molecular isoform of hCG recognized by the B152 monoclonal antibody.

Further, the present invention provides a method for detecting non-trophoblast malignancy in a sample comprising: (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample; and (d) comparing the amount of early pregnancy associated molecular isoform of hCG in the sample determined in step (b) with the amount of early pregnancy associated molecular isoform of hCG in the sample determined in step (c), wherein a positive detection of early pregnancy associated molecular isoform detected in step (b) and a relative absence of the early pregnancy associated molecular isoform of hCG detected in step (c) indicates the presence of non-trophoblast malignancy in the sample.

According to an embodiment of this invention, the antibody is B604, B151, B152 or B207. In an embodiment of this invention, the second antibody is B108, B109. In an embodiment of this invention, the non-trophoblast malignancy is ovarian malignancy or prostate malignancy.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

Finally, the present invention provides a method for detecting gestational trophoblast disease in a sample from a subject comprising (a) contacting a sample with an antibody which specifically binds to the early pregnancy associated molecular isoform of hCG under conditions permitting formation of a complex between the antibody and the early pregnancy associated molecular isoform of hCG; (b) contacting the sample with a second antibody which specifically binds to intact non-nicked hCG without substantially cross-reacting with said antibody under conditions permitting formation of a complex between the antibody and the early pregnancy associated molecular isoform of hCG; (c) measuring the amount of complexes formed, thereby determining the amount of the early pregnancy associated molecular isoform of hCG in the sample due to binding with the first antibody, and late pregnancy associated molecular isoform of hCG in the sample due to binding with the second antibody; (d) determining the ratio of early pregnancy associated molecular isoform of hCG to late pregnancy associated molecular isoform of hCG in the subject; and (e) comparing the ratio of early pregnancy associated molecular isoform of hCG to late pregnancy associated molecular isoform of hCG in the sample determined in step (c) over time, wherein a continuing high ratio of early pregnancy associated molecular isoform of hCG to late pregnancy associated molecular isoform of hCG in the sample determined in step (c) indicates the presence of gestational trophoblast disease in the subject.

In an embodiment of this invention, the antibody is B604, B151, B152 or B207. In another embodiment of this invention, the second antibody is B108, B109. In an embodiment of the present invention, the gestational trophoblast disease is choriocarcinoma or hydatidiform mole.

According to an embodiment of this invention, the sample is a urinary sample or a blood sample. In one embodiment of this invention, the sample is an aggregate sample taken from at least two consecutive days. In an embodiment of this invention, the sample is a spot urine sample, a first morning void urine sample, or an aggregate sample of the first morning void urine samples for at least two consecutive days. In one embodiment of this invention, the antibody is labeled with a detectable marker. In an embodiment of this invention, the detectable marker is a radioactive isotope, enzyme, dye, magnetic bead, or biotin. In a preferred embodiment, the radioactive isotope is $I^{125}$.

As described herein below, unexpected isoforms of hCG are produced during normal early pregnancy. Using an in vitro bioassay, it appears that these isoforms have enhanced potency for signal transduction. These isoforms can be measured using the novel sensitive, immunoassay described herein. This can help predict pregnancy outcome where one cause of early pregnancy loss is failure to produce the isoform of hCG of higher potency produced by successful pregnancies. This enables physicians to intervene to sustain a failing pregnancy. Identification of the nature of the hCG isoform required might provide the proper reagent needed to sustain pregnancy.

New antibodies for measurement of nicked forms of hCG described herein below were developed based on the hypothesis that forms of hCG, which have greatly reduced bioactivity, contribute to early pregnancy loss (EPL), due at least in part to diminished biopotency. Evidence was found that the hCG that appears in EPL patients displays reduced biological activity. However, it was determined that the cause of the reduced bioactivity is not the presence of nicked hCG in EPL patients. Instead, the hypothesis is that patients that carry pregnancies forward produce an isoform of hCG with enhanced bioactivity. The instant invention describes a unique immunochemical assay to measure this unexpected and previously uncharacterized isoform of early pregnancy hCG directly in clinical samples of blood and urine. One of the antibodies developed reacted against a nicked form of hCG isolated from a choriocarcinoma patient, was not specific for a nicked form of hCG but appeared to discriminate among carbohydrate variants of hCG. This antibody, designated B152, appears to preferentially bind hCG forms from choriocarcinoma patients. In studying the content of hCG isoforms during pregnancy, the unique and unexpected observation was made that B152 in the first four weeks of pregnancy measured much higher quantities of an isoform of hCG as compared to the standard hCG isoforms measured by the usual heterodimeric hCG assays exemplified by a previously decribed B109 based assay. In fact, in early pregnancy (days 9, 10, 11 postovulation) B152 measured as much as 20-fold more hCG, than did another monoclonal antibody, B109. Later in pregnancy, the B152 isoform declines and is lower in third trimester pregnancy urine than the standard isoforms measured by B109. A further striking observation was that in very early pregnancy, a high B152/B109 ratio correlates with a successful pregnancy outcome while a low ratio correlated with pregnancy loss. This discovery is important as the potentially overlooked isoforms of hCG described herein during pregnancy may be predictors of successful pregnancy outcome. Such an assay has wide medical applications and provides a clinician with opportunity to intervene very early in pregnancy if the assay indicated that the pregnancy appeared troubled.

An antibody, designated B152, produced by the hybridoma cell line accorded ATCC Accession No. HB-12467, generated against a nicked form of hCG isolated from a choriocarcinoma patient, but not specific for the nicked isoform of hCG is able to discriminate among the carbohydrate variants of beG. B152 is specific for an early pregnancy associated molecular isoform of beG. In the first four weeks of pregnancy, this isoform is detected at much higher levels than the hCG isoforms detected by the standard hCG assays, exemplified by a previously described B109-based assay. Later in pregnancy, the B152 isoform declines until by the third trimester it is detectable at levels below that of the standard hCG isoforms in pregnancy urine.

Antibodies specific for hLH beta core fragment some of which are referred to in the present application, have been detailed in the related co-pending U.S. application Ser. No. 08/763,669 filed Dec. 11, 1996, the content of which is hereby incorporated by reference. In particular, related co-pending U.S. application Ser. No. 08/763,669 filed Dec. 11, 1996, describes monoclonal antibody designated B505 which is produced by the hybridoma cell line accorded ATCC Accession No. 12000 and details methods for its production and use, which is hereby incorporated by reference.

This invention is illustrated in the Experimental Details section which follows. These sections are set forth to aid in an understanding of the invention but are not intended to, and should not be construed to, limit in any way the invention as set forth in the claims which follow thereafter.

The hybridoma cell line B152 was deposited pursuant to and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Vir. 20110-2209 on Feb. 3, 1998 under ATCC Designation No. HB12467. Likewise, the hybridoma cell lines producing the antibodies B207, B108 and B109 were also deposited pursuant to and in satisfaction of, the requirements of the Budapest Treaty with the ATCC, on Apr. 4, 2000 under ATCC Designation Nos. PTA-1626, PTA-1625 and PTA-1624, respectively. All restrictions upon public access to these deposits shall be removed upon the grant of a patent on this application and the deposits shall be replaced if viable samples cannot be made by the depository named hereinabove.

EXPERIMENTAL DETAILS

Example 1

Antibodies to and Analysis of Molecular Isoforms of hCG in Early Pregnancy

Introduction

Almost all investigations of the incidence of early pregnancy loss (EPL), either in normal populations or in-populations at risk as a consequence of exposure to putative reproductive toxins (Hakim, R. B., et al., 1995; Lasley, B. L., et al., 1995) use assays for heterodimeric, non-nicked hCG or combination assays which include free beta subunit and beta core fragment of hCG. One concern about the forms of hCG to include in the measurement in EPL was heightened with respect to the nicking phenomenon described above. Because nicked hCG molecules are not measured by the antibodies employed in most EPL studies, the incidence of EPL is presumably underestimated by an amount proportional to the extent of nicking in the urinary molecule. Another concern of significant importance was a determination of the nature of the "hCG like" immunoreactivity in the urine in the periovulatory surge of the menstrual cycle (O'Connor J., et al., 1995). Recent reports have confirmed the existence of and documented the structure of a sulfated form of hCG produced in the pituitary (Birken, S., et al., 1996b). There is a pulsatile secretion of hCG in both men and non-pregnant women. (Odell, W. D.; Griffin, J., 1989 and Odell, W. D.; Griffin, J., 1987). The presence of a non-pregnancy associated form of sulfated hCG of pituitary origin, peaking at ovulation and perhaps persisting into the luteal phase, could potentially interfere with the accurate estimation of EPL.

Unappreciated isoforms of hCG in blood and urine very early in pregnancy may be more potent in vivo than the forms of hCG produced later in pregnancy. The absence of such isoforms may be one cause of early pregnancy loss. A sensitive and specific immunoassay system was designed and made to measure unique early pregnancy associated molecular isoforms (EPMI) of hCG. These isoforms, likely to differ by carbohydrate composition, are predictive of a successful pregnancy outcome. When these early pregnancy associated molecular isoforms of hCG are absent or present in low concentration, the pregnancy may be lost very early and be observed as only a "chemical" pregnancy. These hCG isoforms may resemble the forms of hCG produced in some choriocarcinoma patients from which the immunogen used to produce monoclonal antibody B152 was derived as described herein below. The isoforms resemble those from trophoblastic disease not in terms of nicking or intact peptide chains but likely in carbohydrate content. The present invention describes that the molar ratio of B152 to B109 epitopes are predictive of a successful pregnancy or a loss. Three categories of pregnant patients were analyzed: (a) normal pregnant women, (b) women who experience recurrent abortions, (c) women undergoing embryo implantation.

It is possible to determine the hCG isoforms present in the blood and urine of women who have a history of recurrent spontaneous abortion and a similar analysis of women undergoing embryo implantation. The combined EPL and spontaneous abortion rate in healthy populations is 31%. Subjects who experience three consecutive recurrent spontaneous abortions have a 32% risk of sustaining another (Hill, J. A.; Anderson, D. J., 1990). In in vitro fertilization IVF pregnancy, the loss rate is 70% with non-donor sperm and 50% when donor sperm is used. Delineation of pregnancies with a negative outcome from pregnancies with a positive outcome can be based on differences in the concentrations of EPMI hCG isoforms (i.e. as differences in the B152/B109 ratio in patients). In addition, specimens from gestational trophoblastic disease (GTD) can be used to discriminate between GTD and normal pregnancy.

Results

In vitro Bioassay for hLH/hCG

Figure 1:
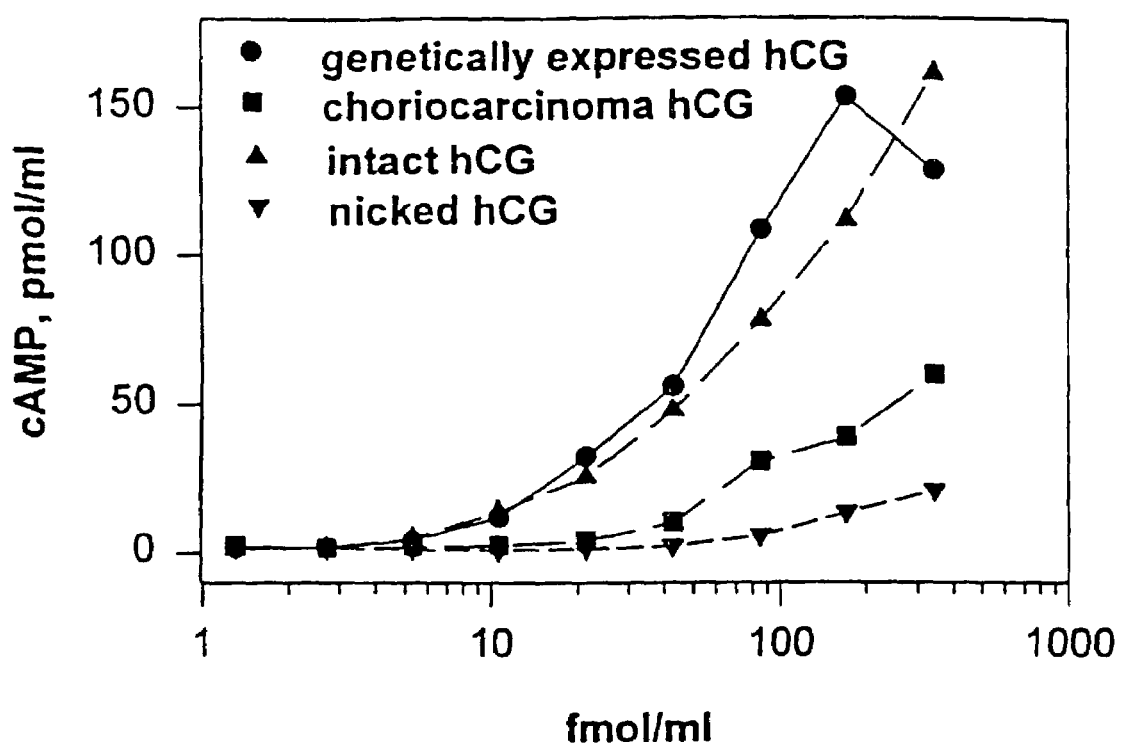
FIG. 1
Figure 3A:
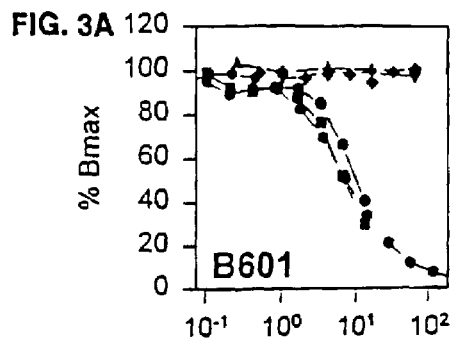
Figure 3B:
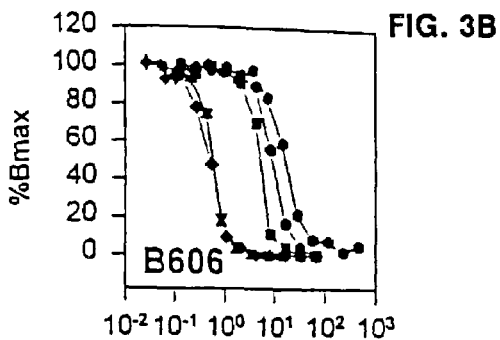
Figure 3C:
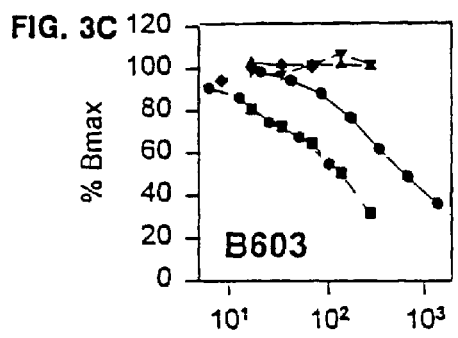
Figure 3D:
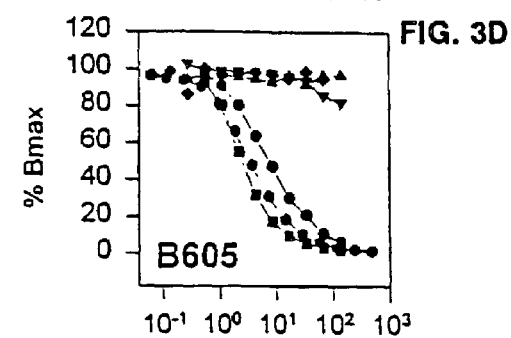
Figure 3E:
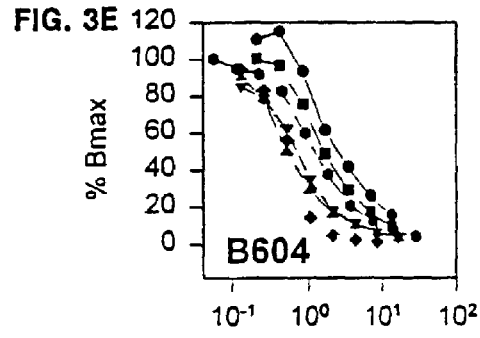
Figure 3F:
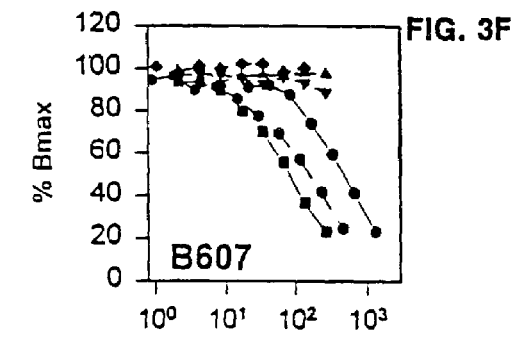
Figure 3G:
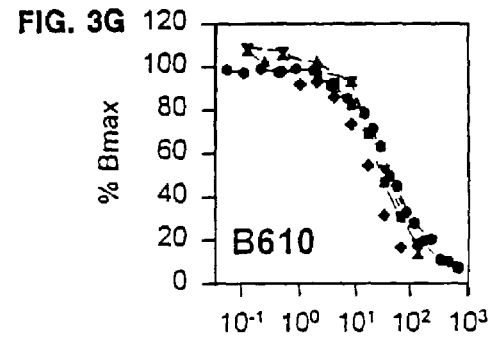
Figure 3H:
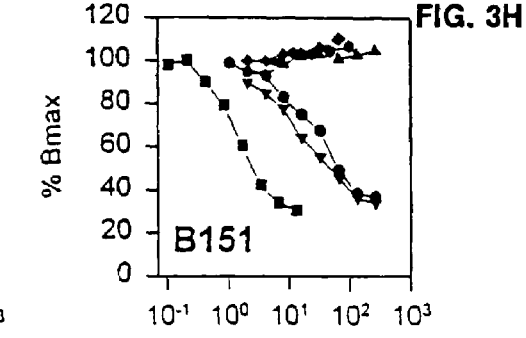

An hCG bioassay was constructed employing CHO cells expressing functional human LH/CG receptor. FIG. 1 illustrates the differences in vitro in biological activity between nicked and non-nicked hCG as measured by this assay. This system, has been used to evaluate the activity of pituitary and placental hCG (Birken, S., et al., 1996b). Preparations of hCG were tested for nicked and non-nicked molecular isoforms of hCG in a second recombinant bioassay system (Ho, H-H., et al., 1997). Similar results were obtained in both systems.

Normal pregnancy values compared with EPL values. Results indicated that nicked hCG is not a significant molar constituent of either early pregnancy or EPL. Data indicated that biological activity is not correlated with nicked hCG, but is instead ascribed to a form of hCG recognized by the B152 monoclonal antibody—an early pregnancy associated molecular isoform of hCG (EPMI hCG). It has been established that there is diminished hCG bioactivity associated with EPL as compared to early normal pregnancy (Ho, H-H., et al., 1997). Thus, diminished hCG biological activity is a factor in EPL as a consequence of a heretofore unappreciated isoform of hCG—an early pregnancy associated molecular isoform of hCG.

hCG Urinary Analytes. Metabolites of hCG and hLH were studied in a variety of states (Birken, S., et al., 1996a). One study indicated a 31% pregnancy loss (Zinaman, M J, et al., 1996) while another indicated a 17.4% rate of early pregnancy loss based on hCG assays (Ellish, N. J., et al., 1996). It is known that hCG and hCG beta core can be readily transferred from the uterus to the circulation even in the absence of implantation (Chang, P. L., 1997). The molecular spectrum of hCG urinary analytes in EPL cycles, normal conceptive cycles and non-conceptive cycles has been evaluated. The study design and demographics of the investigation have been described (Ellish, N. J., et al., 1996).

Briefly, three urine specimens per cycle, corresponding to days 9, 10, 11, post calculated day of ovulation were collected and analyzed in a screening assay (the "combo") which simultaneously detects intact, non-nicked hCG, hCG free beta subunit, and hCG beta core fragment. Individual determinations for each of these analytes, as well as for nicked hCG, and the form of intact hCG detected by monoclonal antibody B152 (EPMI hCG) were performed on these specimens. In addition, since the concentration of luteal phase hLH urinary analytes is a concern because of cross-reaction in hCG assays, levels of intact hLH, hLH free beta subunit and hLH beta core fragment were determined in the normal pregnancy cycles and the non-conceptive cycles. Table I summarizes the characteristics of immunometric assays employed.

TABLE I

Assay format and specificity

| Assay format | Primary analyte | % cross-reactivity |
| --- | --- | --- |
| B109-B108* | intact non-nicked hCG | 0% |
| B201-C104* | hCG free beta (non-nicked + nicked) | 10% nicked hCG |
| B210-B108* | hCG beta core fragment | 2% hLH beta core fragment |
| B151-B207* | hCG nicked | 23% hCG nicked free beta; 14% hCG non-nicked; 14% hCG free beta; 14% hLH; 8% hLH free beta |
| B151-B604* | hCG nicked | 3.7% hCG nicked free beta; 2.5% hCG non-nicked; <0.01% hCG free beta; <0.01% hLH; <0.01% hLH free beta |
| B152-B207* | hCG non-nicked and nicked (pregnancy and C5), hCG free beta nicked and non-nicked (pregnancy and C5), hLH, hLH free beta | 31% hCG nicked (C5); 100% hCG free beta nicked (from C5); 25% hCG nicked (pregnancy); 79% hCG nicked free beta (pregnancy); 50% hCG (pregnancy); <1% hCG free alpha; <1% hCG beta core fragment; 27% hLH; 18% hLH free beta; 3% hLH beta core fragment |
| KB12-A201 | hLH | 0% hCG |
| B505-B503* | hLH beta core fragment | 0% hCG |
| KB21-KB31* | hLH free beta | 29% hLH intact |

The results indicate that nicked hCG does not constitute a significant mole fraction of urinary hCG immunoreactivity in either EPL or early normal pregnancy. In addition, there is a substantial excretion of hCG free beta subunit in some subjects in both pregnancy and EPL. Further, both EPL and normal pregnancy cycles variably express all of the measured analytes. Although both the incidence and level of expression are different between EPL's and normal pregnancy, there is no hCG related analyte unique to either state. There was, however, a clear difference between the hLH associated analytes in the control population (non-conceptive cycles) and the normal pregnancy group. Virtually all of the non-pregnancy cycles expressed hLH free beta subunit and hLH beta core fragment while only a third of the conceptive cycles had detectable levels of either analyte. Intact hLH proved to be a minor constituent of the hLH profile in both groups.

These findings demonstrate both the necessity of measuring hCG beta core fragment in the detection of EPL, and also of making sure that the hCG beta core assay does not cross-react with beta core hLH, which is demonstrated to be present in that part of the luteal phase where EPL measurements are performed. The data is summarized in FIG. 2.

Statistical analysis was performed after transformation of analyte values to mole fractions so as to produce a more useful analysis due to the wide excursion of hCG analyte values among groups. The mole fraction data were evaluated by discriminant analysis and by a mixed effects model incorporating LMP (last menstrual period date). The discriminant analysis was performed both with and without "outliers" (defined as values greater than two standard deviation from the mean) removed. Both approaches produced similar results.

A quadratic discriminant analysis based on a cross-validation method in order to minimize bias correctly classified 91% of the normal pregnancy subjects and 80% of the EPL subjects.

The mixed effects analysis, testing for interactions between mole fraction of analyte and time since LMP found no significant time or group (EPL vs. normal) effects in the intact hCG assay. In the free beta subunit of hCG assay, there is a significant group effect but no time trend. In both the hCG beta core fragment measurement and the B152 measurement, both the hormone levels and the time trend from LMP were significantly different between the EPL and pregnancy groups. This study produced several important findings. It defined the spectrum of analytes which in both early pregnancy and EPL, thereby resolving the issue of which hCG analytes to measure in epidemiological studies in which EPL is the end point determination. More importantly, it illustrated for the first time that there are significant differences both in the pattern of analytes and the time course of their appearance between early normal pregnancy and EPL. This observation facilitates very early prediction of a distressed pregnancy by urinary hCG measurements at a time which would permit therapeutic intervention.

Nicked hCG. Several reports concerning the concentrations of nicked hCG during pregnancy and other states (Hoermann, R., et al., 1994; Cole, L. A., et al., 1993) are based on immunoassays using subtractive manipulations; subtracting results of one assay from that of a second assay to calculate the analyte. Such methods yield erroneous results. Specifically, obtaining values for nicked hCG by subtracting the values from an assay which does not recognize nicked hCG from an assay indifferent to nicking is not valid. The problem is that this approach will not work unless the epitopes detected in both assays are identical. This is apparent from the following data. For example, subtracting the hCG isoforms measured by the B109-B108*, standard non-nicked hCG assay, from the hCG concentrations measured by the new hCG assay which is oblivious to nicking, B152-B207*, does not yield the quantity of nicked hCG present but actually detects new isoforms of hCG not related to nicking of the polypeptide chain. Likewise, use of a scavenger antibody to remove interfering analytes can be effective but introduces inaccuracies in measurements as detailed below. In summary, a significant number of incorrect reports have been placed into the literature purporting to measure nicked hCG during pregnancy while little or none of this material is found during pregnancy using the specific assay systems developed and described herein.

Antibody production. The immunogen for the production of antibodies to nicked hCG was purified from a pool of normal pregnancy urine by a methodology previously described (Birken, S., et al., 1993). Following a standard procedure for hybridoma production (O'Connor J. F., et al., 1994), a total of seven monoclonal antibodies to normal pregnancy nicked hCG, and B151, a nicked hCG specific antibody derived using a choriocarcinoma derived 100% nicked hCG as immunogen, were produced and characterized. B152 (not shown in Table II) raised against the same immunogen as B151, recognizes a novel isoform of hCG associated with early pregnancy—designated herein, EPMI.

After evaluation of all the combinations of nicked hCG monoclonal antibodies, the assay configuration which displayed the best sensitivity and specificity characteristics proved to be B151, a nicked specific monoclonal antibody derived from the C-5 (choriocarcinoma hCG) immunization as the capture antibody and B604, a monoclonal antibody derived from immunization with the nicked hCG fraction purified from normal pregnancy urine, as detection antibody. The characteristics of the immunometric assay employing these two monoclonal antibodies are detailed in Table I (B15-B604*). This assay configuration provided a 2.5% cross-reactivity with intact, non-nicked hCG and 3.7% cross reactivity with nicked free beta subunit.

Table III details findings with respect to the content of urinary nicked hCG in normal pregnancy, ectopic pregnancy and spontaneous abortion, presented as a function of gestational age. The concentrations of non-nicked hCG are presented in the range of pmol/mg creatinine and those for nicked hCG are in fmol/mg creatinine. The assay for the nicked hCG has good but not absolute specificity (2.5% cross reaction with non-nicked hCG). Thus, nicked hCG does not constitute a substantial mole fraction (i.e. <5%-6%) of intact hCG immunoreactivity. A close correlation between blood

TABLE II

Characteristics of monoclonal antibodies

| Antibody | B601 | B603 | B604 | B605 | B606 | B607 | B610 | B151 |
|---|---|---|---|---|---|---|---|---|
| $K_a$, $M^{-1}$ | $5.3 \times 10^8$ | $8.9 \times 10^6$ | $1.2 \times 10^9$ | $1.4 \times 10^9$ | $*3.1 \times 10^8$ | $1.4 \times 10^7$ | $4.6 \times 10^7$ | $8.0 \times 10^8$ |
| Isotype | IgG1, κ | IgG1, κ | IgG1, κ | IgG1, k | IgG1, κ | IgG1, κ | IgG1, κ | IgG1, κ |

*to nicked hCGβ

Table II presents the binding constants and isotypes and FIG. 3 illustrates the specificity of these antibodies towards various hCG and hLH related analytes. It was found that in general, although it is possible to develop monoclonal antibodies with a primary specificity towards normal pregnancy nicked hCG, these antibodies tended to also cross react with hLH. It appears that nicking of the hCG molecule alters its conformation in such a way that epitopes common to both hLH and hCG are exposed.

and urine values for nicked hCG, indicating that the low level of nicked hCG found in urine is therefore not a consequence of preferential renal processing of circulating nicked hCG into smaller urinary molecular fragments. Coupling these observations with the very low incidence of expression of nicked hCG in the early normal pregnancy or EPL discussed previously, it is apparent that nicked hCG does not constitute a major constituent of urinary hCG in the first or second trimester of pregnancy.

TABLE III

Urinary Nicked and Non-nicked hCG in Pregnancy

| Diagnosis | Age (weeks) | n | (+) nhCG assay | nicked hCG fmol/mg crt median | nicked hCG fmol/mg crt range | Non-nicked hCG* pmol/mg crt median | Non-nicked hCG* pmol/mg crt range |
|---|---|---|---|---|---|---|---|
| normal pregnancy | 1.7-4.0 | 42 | 15 | 23 | 3-222 | 2.7 | 0.2-88.5 |
| | 5-6 | 9 | 3 | 140 | 111-842 | 6.1 | 1.6-871.8 |
| | 10.6-14.9 | 17 | 17 | 971 | 36-6065 | 214.0 | 64.8-7184.5 |
| | 15-21.7 | 81 | 81 | 113 | 6-4718 | 60.5 | 7.3-2663.5 |
| | 28.1-39 | 6 | 6 | 46 | 28-93 | 30.2 | 16.5-138.1 |
| ectopic pregnancy | 2.3-4.3 | 9 | 4 | 6 | 3-20 | 3.6 | 1.2-6.7 |
| spontaneous abortion | 1.9-4.1 | 12 | 3 | 4.5 | 4-11 | 0.8 | 0.2-2.3 |

*Note that the concentration of non-nicked hCG is expressed in pmol/mg crt and nicked hCG in fmol/mg crt,
(+) = positive,
n = number of samples analyzed,
crt = creatinine In order to be certain that some matrix effect was not interfering with detection of nicked hCG, its recovery from spiked hCG free serum and urine was evaluated. Recovery ranged from 69%-83% in serum and around 72% in urine. It became evident from recovery studies of nicked hCG in spiked pregnancy serum that the recovery determination was a function of the concentration of intact hCG in the specimen. (See FIG. 4A)

Although a scavenger antibody does function to remove a substantial part of the interfering analyte (hCG), which is usually present in large excess (as in pregnancy), it also alters the observed recovery of nicked hCG, due presumably to some cross-reactivity of the interfering hCG in the assay (FIG. 4B, FIGS. 5A and 5B).

These studies indicate that the quantities of nicked hCG are too low when compared with those of non-nicked hCG, to be of physiological significance. Furthermore, measurement of these small quantities in the presence of large excess of the non-nicked hCG isoform, even with a specific assay, are not accurate, due to intact hCG interference in the nicked hCG assay.

hCG-like immunoreactivity in periovulatory urine. Most of the "hCG like" immunoreactivity in urine was determined to be associated with hLH beta core fragment (hLHβcf). An assay (Kovalevskaya, G., et al., 1995) was developed which was capable of discriminating between the highly homologous hLHβcf and hCG beta core fragment (hCGβcf). This has permitted for the first time the dissection of the hLH/hCG immunoreactivity signal around ovulation. It was found that the predominant urinary molecular form in the periovulatory period was hLHβcf, with concentrations which are virtually an order of magnitude higher than either intact hLH or hLH free beta subunit (hLHβ). The contribution of hCG analytes, as judged by hCGβcf measurement is small in comparison to hLHβcf (O'Connor, J., et al., 1997).

Stability of Nicked hCG in Blood and Urine. Three types of stability experiments were performed. The stability of nicked hCG itself, purified from pregnancy urine was evaluated in buffer. The changes in measured endogenous nicked hCG in urine and serum pregnancy pools was also evaluated because of possible "nicking enzymes" in biological fluids reported by other investigators (Kardana, A., 1996).

Sera and urine of pregnant women at different gestational ages were pooled and sodium azide (0.1%) was added. Urine pH was adjusted to pH 7 with 1M tris HCl. Aliquots stored at −80° C. served as control samples. Other aliquots were incubated at 4° C., 20 C. and 37° C. for extended time periods. After each time period the samples were stored at −80 C. All of the specimens were analyzed in the same assay. Nicked hCG in buffer (PBS/bovine IgG, sodium azide) which was treated with the same incubations and was analyzed in B151-B604* and B201-C104* assays.

With respect to stability in the buffer, two effects were noted. At 37° C., there was a rise in hCG free beta subunit (hCGβ) due to the anticipated heat related increase in dissociation of the intact hCG molecule. Additionally, there was a decrease in nicked hCG over time after 20 hours of incubation, regardless of storage temperature, this occured even when there was no dissociation, as evidenced by hCGβ analysis. The effect was more pronounced at 20° C. and 37° C. than at room temperature. During a 70 hour time period the concentration decreased to about 50% of the initial value at 20° C. and 37° C. and to about 60% at 4° C. Although at elevated temperature, dissociation appears to be the predominant cause, at lower temperatures this is not the case, and the loss of nicked hCG immunoreactivity must be ascribed to destruction of the B151 epitope.

Endogenous pregnancy specimens of serum and urine stability determinations are confounded by the presence of a great excess of intact, non-nicked hCG, from which the nicked variant presumably arises. In both serum and urine, the apparent concentrations of nicked hCG remain relatively constant at 4° C., but increases with increasing time of exposure to elevated temperature. It appears from these data that the net rate of formation of nicked hCG (or increase exposure of nicked epitopes) as a result of heating is somewhat greater than the rate of destruction of nicked hCG resulting in an apparent increase in nicked hCG levels over time.

Example 2

B152/B109 Ratio Predicts Pregnancy Outcome

Figure 6:
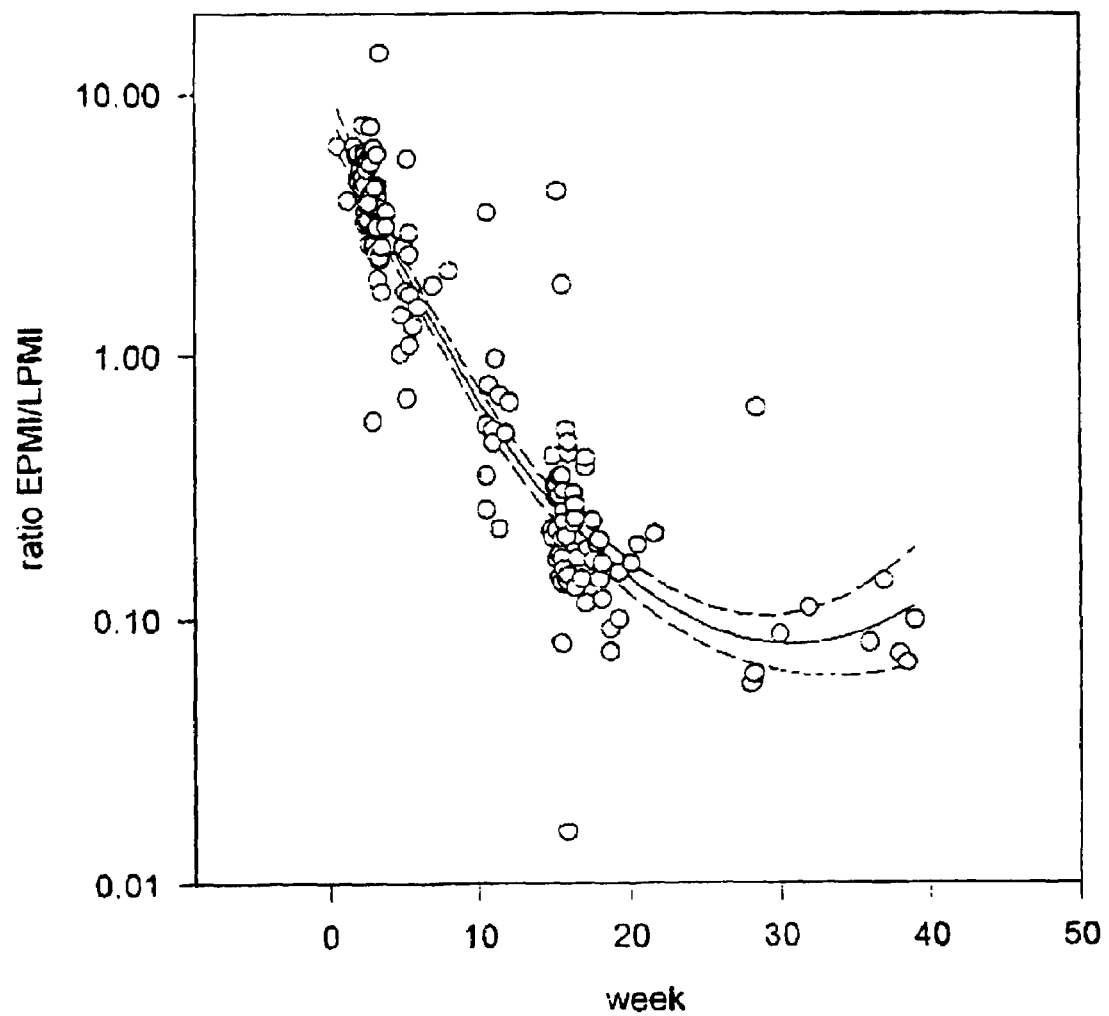
Figure 11:
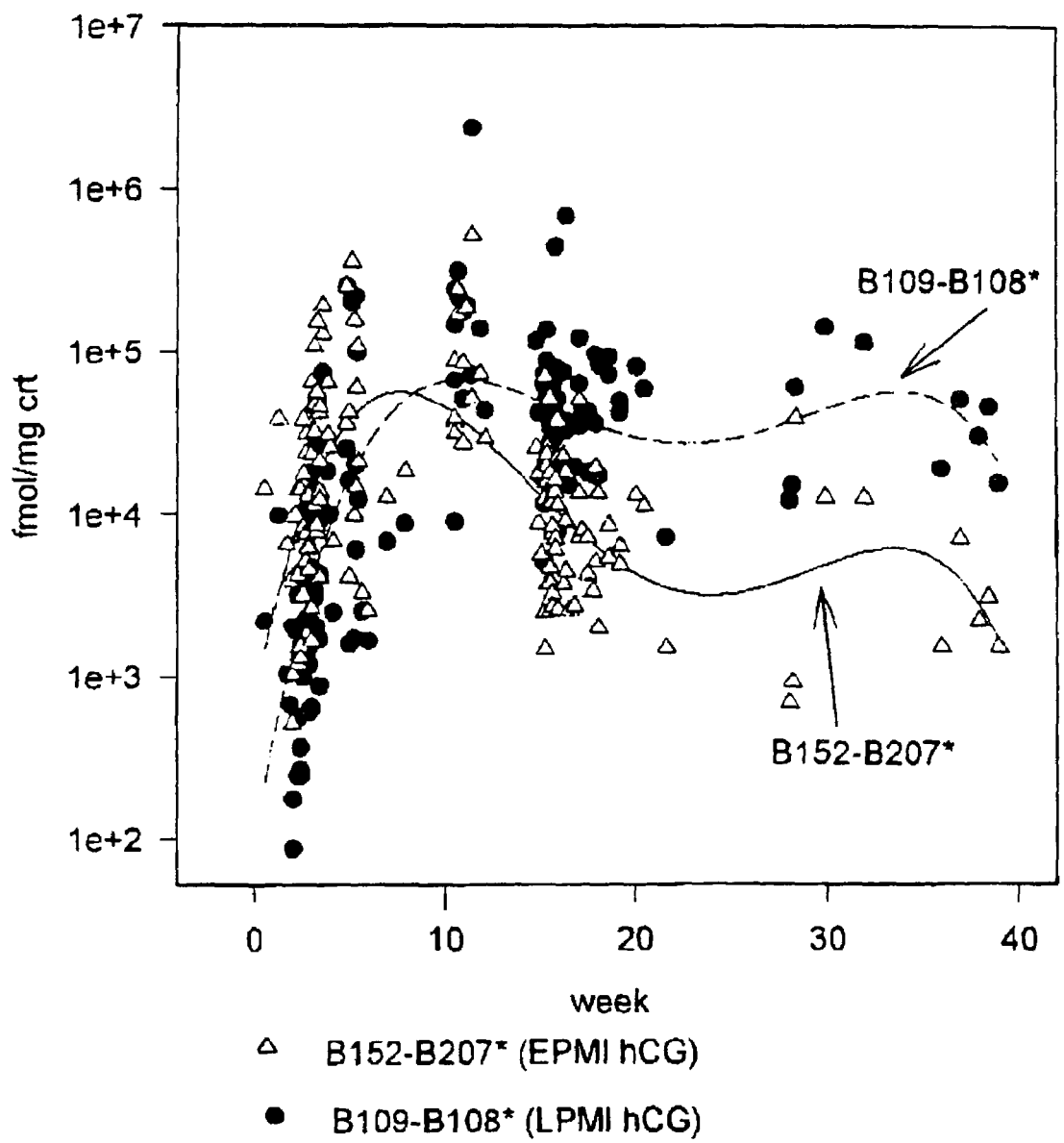

B152/B109 immunoreactivity ratio as a function of gestational age. A total of 159 urine samples from normal pregnancies of known gestational age were assayed for intact hCG in the B109-B108* and B152-B207* assay configurations (See Table I). Over the gestational age range from 1-2 weeks to 40 weeks, the ratio of hCG isoforms as measured by the two assays decreased by nearly two orders of magnitude, with the greatest change occurring in the first fifteen weeks of gestation. See FIGS. 6-11. FIG. 6 presents the second order regression curve ($r=0.92$) and 95% confidence intervals of the B152/B109 hCG isoforms ratio in urine as a function of gestational age (see also FIG. 11).

Figure 7:
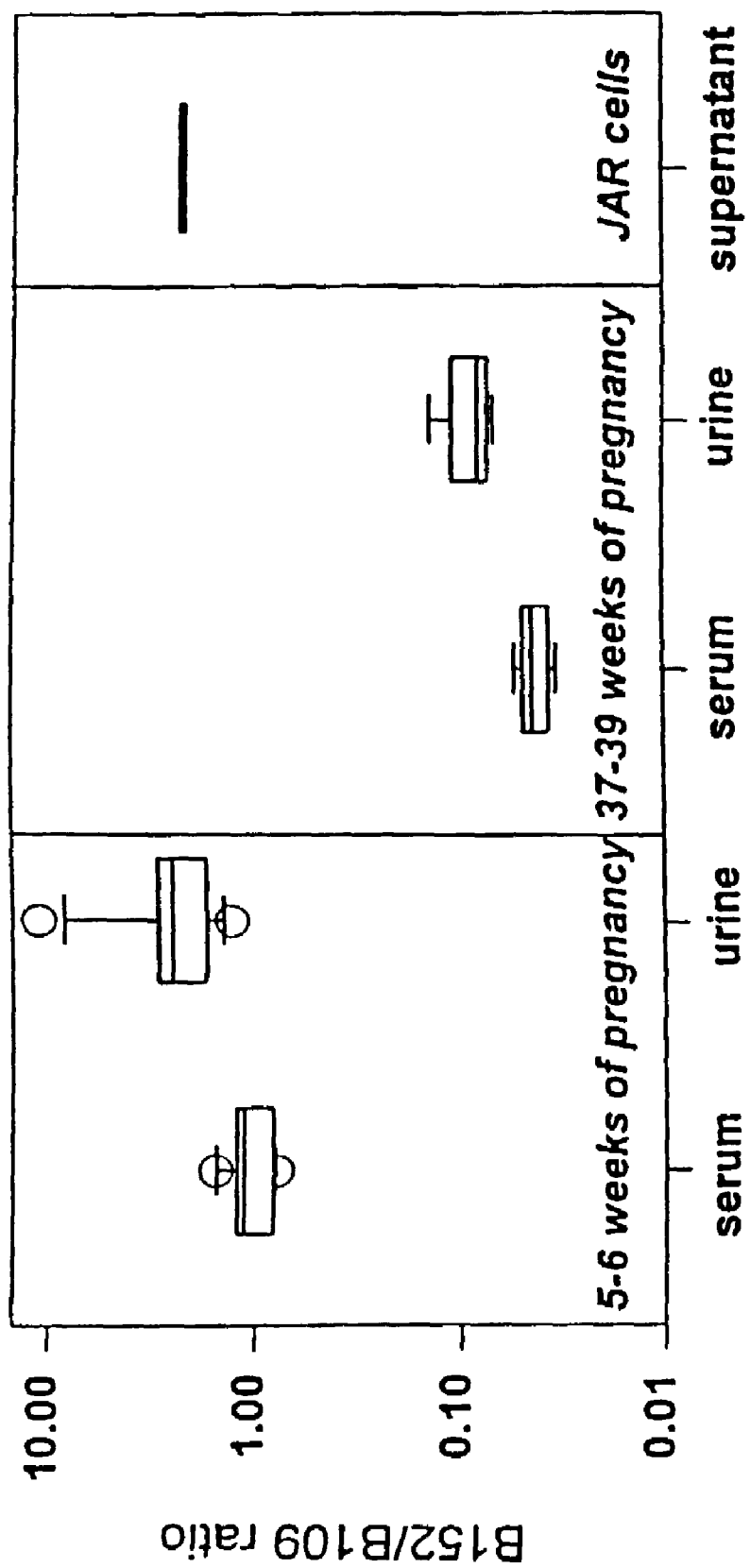

Analysis of matched blood and urine specimens in the first 5-6 weeks of pregnancy (n=10) and specimens obtained in the late third trimester, just prior to caesarian section (n=5) displayed a similar B152/B109 ratio inversion in serum as was observed in the urine from the same subjects. This data strongly suggests that the same change in the distribution of hCG isoform prevails in serum as observed in urine throughout the pregnancy (FIG. 7). It is of interest to note that the ratio of the two hCG forms in the JAR choriocarcinoma cell line, with a B152/B109 ratio of approximately two, supports the hypothesis that the form of hCG produced in early normal pregnancy differs in carbohydrate structure from that produced later in pregnancy and in fact may more closely resemble the hCG produced in trophoblastic malignancy which is characterized by a difference in the carbohydrate portion of the molecule as compared to the hCG derived from pregnancy. It has been reported that the hCG produced by choriocarcinoma has a higher biological activity than does the hCG from normal pregnancy (Wide, L., and Hobson, B., 1987). Studies indicate that early pregnancy isoforms of hCG have different biological activities when pregnancies are lost as compared to pregnancies that continue (Ellish, N. J., et al., 1996). Thus, the B152-based is a sensitive immunoassay to detect critical isoforms of hCG.

Chromatography of First Week of Gestation Pregnancy Pool. In order to determine whether the B152-B207* assay recognized other forms of hCG associated immunoreactivity in addition to the intact hCG molecule, specimens were pooled. FPLC on tandem Superose 12 columns followed by immunoassay of the fractions for all of the characterized forms of hCG revealed that only the intact hCG molecule (or hCG free beta subunit) gave a signal in this assay (See FIG. 8). There were no lower molecular weight fragments identified by the B152-B207* assay. The hCG free beta analyte was measured in the 159 urines described in FIG. 6 and was found to make a negligible contribution to over all hCG immunoreactivity in these specimens.

Molecules recognized by monoclonal antibody B152 in urine and pituitary extracts. In order to define the nature of the hCG isoforms recognized by B152, high resolution gel filtration columns of both pituitary extracts and postmenopausal urine concentrates were used (See FIG. 8). The rationale for use of pituitary extracts is to determine cross-reactive molecules, specifically those which are glycosylated, which are plentiful in pituitary which contains the entire family of glycoprotein hormones, hLH, hTSH, and hFSH as well as free subunits and the pituitary form of hCG. Two peaks are detected in both of these cases. Only one peak was detected in similar studies of pregnancy urine concentrates as described earlier. In the pituitary, it is likely that the larger molecule is pituitary hCG (70K) while the smaller sized molecule is hLH. Since hLH is present at 100× or so as compared to pituitary hCG, the apparent similar concentration of immunoreactivity indicates that B152 has reduced cross-reactivity to hLH as compared to hCG. Likewise, both hCG and hLH occur in postmenopausal urine, again with much more hLH than hCG and the B152 pattern is similar to that of the pituitary extract. These results show that B152 is generally hCG specific except for cross reactivity to hLH (as shown by standard cross-reaction studies in Table I) and that its carbohydrate specificity is both to the protein portion as well as to the carbohydrate moeities of hCG (and to a lesser extent of hLH) since it does not react with the multitude of other glycoyslated proteins present in the pituitary nor with those in postmenopausal urine except for hCG or hLH-related molecules.

Profiles of B152 immunoreactivity throughout normal pregnancy; correlation with receptor binding and in vitro biological activity. Matched blood and urine specimens are, collected at approximately weekly intervals throughout the duration of gestation (FIG. 7). These specimens are used to evaluate the correlation of assay values with in vitro receptor binding capacity and biological activity and to establish the range of time over which the transition of isoforms occurs in normal pregnancy.

Serum and urine specimens were analyzed using two assays, B109-B108* and B152-B207*, which recognize the difference in molecular isoforms of hCG. See Table. I. The in vitro bioassay for hLH/hCG is described above. (See FIG. 1). Results are indicated in FIGS. 6-11. The immunometric assay employs 96-well microtiter plate technology. The coating antibody, at a concentration determined to provide the most satisfactory combination of sensitivity and range, is applied to the microtiter wells (Immulon IV, Dynatech Laboratories) in carbonate buffer (0.2M, pH 9.5). The plates are incubated with the coating solution at 4° C., overnight, then aspirated, washed with washing solution (0.05% Tween, 0.15N NaCl), and blocked with a 1% solution of BSA (three hours at room temperature). The BSA solution is aspirated and the appropriate hCG standards (200 µL/well), in buffer B (PBS/0.1% bovine IgG/0.1% sodium azide), or in hCG free serum (Chemicon, Inc.), or hCG free urine, as appropriate to the specimen matrix, and specimens are added to the wells. The plates are sealed with plate sealers, and incubated overnight at 4° C. The controls, specimens, and standards are then aspirated, the plates washed 5 times with washing solution, and iodinated detection antibody in buffer B (200 uL/well, 100, 000 cpm/well) added and incubated overnight at 4° C. The wells are again aspirated, washed 5 times with washing solution, separated and counted (Packard Cobra gamma counted). Values are interpolated from a smoothed spline transformation of the count data. This assay procedure, as well as assay validation has been previously reported (O'Connor, J. F., et al., 1988).

Creatinine analysis, when urine values are normalized to creatinine, is performed in a microtiter plate format following a modification of the Taussky procedure (Taussky, H. H., 1954).

EPMI hCG in women with a history of recurrent spontaneous abortion and ectopic pregnancy. This experiment extended the observations of the significant difference in production of the hCG isoform preferentially recognized by the B152 antibody between successful and failing pregnancies. The specimens for this investigation were provided from women who experienced recurrent spontaneous abortions and ectopic pregnancies. Results are indicated in FIG. 10.

EPMI hCG in women undergoing embryo transfer. IVF patients are a group in which the rate of pre-clinical loss is presumably significant; the rate of successful clinical pregnancy in the IVF Program at Columbia University is 30% when non-donor sperm is used and 50% when donor sperm is used. A study on the effect of exposure to electromagnetic fields on EPL incidence with enrolled 650 subjects had approximately 10% daily collectors, the remainder collected 2 urine samples/cycle (first 2 days of menses). Of 167 clinical pregnancies there were 25 clinical losses and 34 putative early pregnancy losses. Of the live births, 7 are daily collectors as are 3 of the clinical losses.

Subjects collect small (5 mL) aliquots of first morning void urine. Urine collection commences three days before embryo transfer (baseline) and continues until the subject is confirmed to be clinically pregnant or not. This determination usually occurs at days 9 and 11 following embryo transfer. Blood specimens are also obtained on these subjects. Matched blood and urine specimens are obtained at various gestational ages. Serial blood and urine specimens Control specimens are obtained from patients who maintain their pregnancy full term. In addition to the B109-B108* and B152-B207* assays for intact hCG, hCGβ and nicked hCG determinations are performed on the serum and urine and additionally the hCGβcf assay on the urine specimens.

Descriptive statistical and graphical methods are used to measures of serum and urine samples from normal healthy pregnancies to identify the distributions a) between patient first trimester average B152 levels, B109 levels and B152/B109 ratio; b) between patient variability in time to B152/B109 ratio reaching 1.00; and c) between patient variability in time to B152/B109 ratio declining by ⅓rd from first trimester maximum levels. The variability in the timing of the crossover in the ratio of these two analytes provides an empirical basis from which to estimate the value of these markers as biochemical signatures of a viable third trimester fetus.

Comparison of the assay profile of healthy normal pregnancies to those of unsuccessful pregnancies from failed IVF implantations, two non-parametric hypotheses are available: 1) the proportion of pregnancies in which the B152/B109 ratio falls below 1.00 is no different in healthy normal and unsuccessful IVF pregnancies; 2) the proportion of pregnancies in which the B152/B109 ratio declines by ⅓rd from first trimester maximum levels is no different in healthy normal and unsuccessful IVF pregnancies. These hypotheses can be tested as a difference between two proportions. For example, a comparison of week 14 vs. week 9, week 13 vs. week 6, week 12 vs. week 5 or week 11 vs. week 4 pregnancies to show a reversal of the B152/B109 ratio in healthy normal pregnancies and unsuccessful IVF implantations, respectively. The power analyses apply to an outcome defined as the time at which the B152/B109 ratio declines by ⅓rd from first trimester maximum levels, although this outcome would necessarily provide earlier detection of pregnancy failure than the reversal of the B152/B109 ratio. Patterns of results less discriminantly different from these indicate a rejection of the dichotomous outcome of B152/B109 ratio reversal as a clinically meaningful marker of pregnancy failure.

Alternatively, the same two non-parametric hypotheses can be recast as parametric hypotheses by considering the timing of the biochemical events within the assay profile of healthy normal pregnancies and unsuccessful pregnancies from failed IVF implantations: 1) the time at which the B152/B109 ratio falls below 1.00 is no different in healthy normal and unsuccessful IVF pregnancies; 2) the time at which the B152/B109 ratio declines by ⅓rd from first trimester maximum levels is no different in healthy normal and unsuccessful IVF pregnancies. Of course, the objective is to provide an empirical basis from which clinicians may counsel their patients. Thus, it is important to adopt a logistic model for this component of the data analysis. With pregnancy success as the outcome, logistic models allow the estimation of the (symmetrical) hypothesis of increase in risk of pregnancy failure for each additional week where either the B152/B109 ratio has failed to decline by one third from first trimester baseline maximum values or the B152/B109 ratio has failed to become less than 1.00 (measured in weeks). The logistic model enables specification of the time at which results indicate a particular pregnancy exceeds an a priori defined likelihood of failure, given assay data regularly available during pregnancy, and allows incorporation of other risks for pregnancy failure in the same data analytic framework to assess the relative contribution of threats to pregnancy loss. The Cox proportional hazard model may be used to examine predictors of the crossover rates. Mixed effects models can also analyze repeated measures of the B152/B109 ratios taken during entire cycles. These models are particularly useful since they allow inclusion of incomplete and imbalance data (i.e. data with missing values and unequal timing of data collection), to estimate effects of time-varying covariates, to model dependency structure of repeated measures and to model possible heterogeneity of the ratio measures within each experimental group.

B152 hCG isoforms isolated from early pregnancy urine and determination of their protein and carbohydrate structures. Using the already developed scheme of concentration and immunoaffinity extraction of urine, hCG molecules are isolated from urine collected from women in early pregnancy for both protein and carbohydrate analyses. According to one approach, molecules are isolated from HPLC fractions, digested with proteases before and after reduction of disulfide bonds, examination of the resultant peptides by mass spectrometry and/or sequence analysis, isolation of carbohydrate moieties after glycosidase digestions and determination of carbohydrate structures by a combination of specific glycosidases and retention times on specialized anion exchange columns as compared to know branch-chain oligosaccharide standards. In a similar approach, the final purification stage for the isolated hCG isoforms is SDS gel electrophoresis. Both protease digests and glycosidase digests are performed on the blotted and cutout band. This method results in greater purity of the protein and less artifactual errors due to contamination by carbohydrates which are not in the purified protein but are derived from outside contaminants.

Carbohydrate compositional analyses and oligosaccharide branched chain identifications. The MALDI TOF mass spectrometric method may be used to confirm oligosaccharide structures by using specific glycosidases on the glycopeptides and determining the change in molecular weight as the sugars are digested off the glycopeptide. Only the hCG beta COOH peptide can be expected to contain O-linked sugar moieties. These are of special interest since it is thought that B152 has significant reaction with this region. The structures of this region can be determined in a similar fashion using enzymes that specifically release O-linked glycans. The O-linked structures has been previously examined using standard reference pregnancy hCG (Cole, L. A., et al., 1985). The O-linked branched chain structure are determined by a similar strategy using the Dionex chromatographic system as well as specific glycosidases on the C-terminal glycopeptides and Mass Spectrometry. In one study (Elliott, M. M., et al., 1997), these techniques were used to elucidate the carbohydrate structures of CR series hCG preparations (standard urinary pregnancy hCG) and compared them to the structures of patient samples such as C5 which was the immunogen employed to generate antibody B152. It was found that C5 contained significantly more mono and tri-antennary (2×mono and 3×tri-structures than the CR preparations) on the N-Asn residues. It was also found that more tetrasaccharide structures were on the hCG COOH-terminal peptide O-Serine residues in the choriocarcinoma hCG isoform than in the CR preparations.

Biological activity and metabolic clearance of hCG isoforms. Biological activity is a function both of molecular structure and half-life in the circulation, which can be influenced by structure. Alterations in carbohydrate/sialic acid content of the glycoprotein hormones are thought to be responsible for the changes in hCG biological/immunological activity observed throughout pregnancy. In addition, signal transduction at the receptor is influenced by the pI of the hCG isoform and the presence or absence of carbohydrate. Thus, it is valuable to examine both receptor binding and biological activity in vitro and, in order to determine the mechanism of action, to distinguish receptor binding and signal transduction as well as relative potency of signal transduction along with in vivo bioactivity determinants such-as circulating half life. Studies, including clearance rates, are performed on B152 hCG isoforms of early successful pregnancy, hCG from third trimester pregnancy, and the reference urinary hCG preparation, CR 127.

Example 3

B152 and B151 Immunoreactivity in Non-trophoblastic Malignancy

With the exception of trophoblastic disease and testicular cancer, hCG is expressed in the blood of about 20% of patients with all other types of cancer (Hussa, R. O., 1987). HCG beta core fragment in the urine has a significantly higher level of expression, especially in gynecological malignancy. Since the B152 antibody was developed to a form of hCG produced in a malignancy, it was of interest to examine the expression of B152 and nicked hCG immunoreactivity (B151) in non-trophoblastic malignancy. Accordingly, blood and urine derived from men undergoing chemotherapy for prostate cancer or women for ovarian cancer were evaluated for the expression of hCG isoforms in plasma and urine. It is significant that in prostate cancer, B152 hCG immunoreactivity is found in the blood and urine of prostate cancer patients in instances when there is no hCG detected by B109-B108*. In ovarian cancer patients evaluated, there is evidence of nicked hCG in the blood, even in the absence of both B109 and B152 immunoreactivity. Neither of the above groups demonstrated the presence of hCG immunoreactivity when the standard pregnancy derived hCG assay was employed. It is reassuring to find that nicked hCG, the existence of which has been documented by several investigators, can be found and reliably measured in a clinical setting.

Experimental Discussion

While it has been found that nicked hCG does not play a significant role in early pregnancy loss, a novel observation was made of previously unknown isoforms of hCG produced during very early pregnancy. In the course of these studies, a potentially important new signal was observed in the urine of women early in pregnancy, namely an epitope of a form of hCG which may indicate the likely success of carrying a pregnancy. Likewise, absence of this signal may indicate that EPL will occur. Since EPL can be a very sensitive marker of environmental toxins (Hakim, R. B., et al., 1995) and is frequently used as an epidemiological marker of exposure, the finding of this epitope provides a powerful tool for monitoring the safety of the environment. In addition, this assay facilitates increasing the success rate of IVF infertility programs since the predictive value of the new measuring system would rapidly indicate successful approaches. Described herein is the novel and completely unexpected finding that successful pregnancies display a high content of unique isoforms of hCG that are maintained for the first few weeks of pregnancy and then rapidly decline as pregnancy progresses. Based on properties of the immunoassay system, it is hypothesized that these hCG isoforms may be hyperglycosylated. This is a striking observation never reported nor suspected earlier. Carbohydrate analyses (Elliot, M., 1997) demonstrate that Cs hCG employed as immunogen for antibody B152, contains two times the monoantennary content and three times the tri-antennary content of branch chain sugars as compared to the CR series of natural pregnancy urinary hCG. In addition, the O-linked carbohydrates are mostly tetrasaccharide instead of disaccharide in C5 as compared to CR 127 hCG. (CR 127 hCG is similar to the WHO preparation, the third international hCG standard, which was CR 119 hCG, prepared by Canfield and Birken twenty years ago but still in use today)(Birken, S., et al., 1991a). B152 recognizes CS hCG much better than nicked CR127 hCG or non-nicked CR 127 hCG (Birken, S., et al., 1993). In addition, JAR cell type hCG is known to contain a similar array of carbohydrate moieties. It was found to be recognized by B152 similar to the early pregnancy isoforms in healthy pregnancies. The observation that the hCG isoform produced by JAR cells in culture (B152/B109 ratio) is similar to that found in early pregnancy hCG isoforms supports the hypothesis that the production of a type of hCG with a particular glycosylation pattern is a prerequisite for a viable pregnancy. This glycosylation pattern is not characteristic of the hCG of later pregnancy.

A variety of pregnancy disorders are testable. One category of patients consists of those women who experience a high rate of recurrent abortions. Even in populations with no known fertility problems, the total rate of pregnancy loss is 32% (EPL plus clinically recognized abortion) (Wilcox, A. J., et al., 1988). The risk of recurrent abortion increases with the number of spontaneous abortions experienced in the past, reaching an incidence of 32% after three consecutive abortions. (Hill, J. A., and Anderson, D. J., 1990). Probable causes of recurrent spontaneous abortion, comprising genetic, infectious, hormonal imbalance, or immunologic factors can be established in less than 60% of all spontaneous abortions, leaving 40+% of spontaneous abortions with a completely unestablished etiology. These facts, taken together with reports establishing that the administration of exogenous hCG can be an effective therapy in subjects with a history of recurrent spontaneous abortion (Quenby, S., and Farquharson, R. G., 1994; Harrison, R. F., 1985) lends support to the hypothesis that a disproportionate production of the ineffective isoforms of hCG in early pregnancy is a causal factor in both early pre-clinical loss as well as in spontaneous abortion.

A second category includes women undergoing embryo transfer. These patients provide several distinct advantages: The patients undergoing this procedure are not treated with crude hCG preparations, making measurement of hCG isoforms easy and decisive since all hCG forms derive from the embryo none from any injected hCG preparations. Second, is the opportunity to monitor the nature of the isoforms from day 9 of a successful pregnancy. Third, is the ability to obtain large volumes of urine to purify the early pregnancy isoforms to determine their structures. Fourth, since pregnancy loss is from 50% to 70% in this population, the loss can be defined as due to lack of the essential hCG isoform recognized by B152 or due to other causes. Comparison of early pregnancies in populations of women not undergoing in vitro fertilization procedures with those undergoing embryo implantation can, thus, assess whether pregnancy loss situations present similar or different patterns of hCG isoforms during the process. The mechanism of pregnancy loss in the general population as compared with the much higher rate of embryo loss in IVF programs may be different. Additionally, it has been established that the hCG produced in choriocarcinoma has differences in carbohydrate structures, sialic acid content and biological activity (Wide, L., and Hobson, B., 1987; Elliot, M., et al., 1997; Hussa, R. A., 1987). Since both the B151-B604* and B152-B207* assays incorporate monoclonal antibodies raised against an immunogen derived from choriocarcinoma, speicmens may be evaluated from patients with gestational trophoblastic disease in order to determine whether the above assays recognize the hCG produced in these conditions with greater sensitivity and specificity than do assays based on the hCG of normal pregnancy, as is apparently the case for the hCG produced in testicular and ovarian cancer.

There are few reports of changes of carbohydrate content of hCG-related molecules during pregnancy. Blithe and colleagues studied free alpha subunit of hCG whose carbohydrate content differs from that of alpha within hCG by additional carbohydrate antennae and fucose. The carbohydrate of free alpha becomes increasingly complex in terms of more branches and higher content as pregnancy proceeds. It has also been reported that the quantity of fucose increased in both hCG and in free alpha as pregnancy proceeded (Skarulis, M. C., et al., 1992). Thus, the literature indicates increasing content and complexity of carbohydrate of hCG and free alpha subunits. However, immunological data using the B152 monoclonal antibody, implies a progression to simpler carbohydrate content during pregnancy. Since the beta COOH-region's O-linked carbohydrates may be involved in the epitope recognized by B152, it is conceivable that the carbohydrate structures of this region may be altered in a different pattern from the N-linked glycans studied by Blithe and colleagues (Skarulis, M. C., et al., 1992; Blithe, D. L., and Iles, R. K., 1995). Data from Skarulis et al. indicate that heterodimeric hCG may contain additional fucose but do not provide data that this late pregnancy hCG becomes hyperglycosylated as does free alpha.

Other studies indicated that the forms of hCG during EPL likely differ in biological activity from those hCG isoforms in successful pregnancies (Ho, H.-H., et al., 1997). The in vitro bioassays employed in those studies are unsuitable for large-scale studies and are not as reliable as the immunoassays described herein. Furthermore, it is likely that in vivo assays may give different results since in vitro and in vivo assays sometimes give completely disparate results. In this case, in vivo and clearance assays are most important in order to identify whether the hCG isoforms are truly more potent in the whole animal and to identify the reasons for the increased potency. Thus in vitro and in vivo bioactivities of the early pregnancy isoforms of hCG are highly significant.

Carbohydrate differences is a widely accepted explanation for variations in biological to immunological ratio such as the forms observed by various studies of EPL (Ho, H.-H., et al., 1997). Various studies (Grotjan, H. R. J., and Cole, L. A., 1989; Hoermann, R., 1997; Stanton, P. G., et al., 1993; Szkudlinski, M. W., et al., 1995, Thotakura, N. R., et al., 1994; Szkudlinski, M. W., et al., 1993), have shown that sialic acid differences are an explanation for such heterogeneity in biological activities of glycoprotein hormones. These studies have also confirmed the dogma that in vitro biological activities can yield the opposite results from in vivo studies because of altered metabolic clearance rates in the latter studies. Thus, more acidic (more highly sialylated) forms of gonadotropins are more biopotent in the whole animal because of prolonged circulating half-lives. The same molecules may appear less potent in in vitro assays due to greater acidity, greater negative sialic acid content. Hoermann et al. (Hoermann, R., et al., 1997) demonstrated the exclusion of many of the acidic circulating hormone forms from the urine, thus, prolonging their half-lives. The pI pattern of normal pregnancy as well as trophoblastic cancer hCG in serum is quite different from that of urine. Since the studies described herein indicate that EPL hCG isoforms have reduced in vitro biological activity, this finding cannot be explained solely by what is known of biological activity and sialic acid content. Early pregnancy isoforms recognized by monoclonal antibody B152 may be more potent in vivo by virtue of prolonged half-life they may then display increased signal transduction at the receptor as well. This may be explained by a hyperglycosylated form of hCG which is not hypersiaylated. In this case, the extra sugar portion would help prolong circulating half-life of a more basic pI form of hCG which also has increased in vitro bioactivity.

Example 4

Diagnosis of Gestational Trophobloast Disease

An important application of the B152 (early hCG isoform)/B109 (late hCG isoform) ratio analysis described herein above is in the very early (and facile) diagnosis of gestational trophoblast disease. Examples of gestational trophopblast disease include choriocarcinoma or hydatidiform mole. In normal pregnancy, the ratio of B152/B109 of the two isoforms of hCG rapidly decreases, eventually inverting. In gestational trophoblast disease including choriocarcinoma or hydatidiform mole, the ratio is initially higher than found in normal pregnancy, but does not diminish during the course of the apparent pregnancy. This approach provides a highly sensitive and specific diagnostic marker for gestational trophoblast disease.

Other pregnancy disorders in which hCG levels are abnormally high or abnormally low include Down's syndrome or other aneuploid pregnancies, ectopic pregnancy, preeclampsia, and intra-uterine growth retardation. Because the hCG production in these conditions is quantitatively abnormal compared with normal pregnancy, an altered ratio of the hCG isoforms identified by B152 (early hCG isoform) and B109 (late hCG isoform) can be detected.

Thus, the dual isoform analysis (B152/B109) further provides a method for diagnosing pregnancy disorders and gestational trophoblast disease.

Experimental Procedures

Hormones. hCG CR127 was prepared and characterized as described earlier (O'Connor et al. 1994, Birken et al. 1991). Nick-free hCG (preparation 814) was separated from parent CR 127 preparation by hydrophobic chromatography. Procedure was a modification of the separation of Phenyl Sepharose described earlier (Birken et al. 1993). CR 127 hCG (26 mg) was dissolved in 0.6M ammonium sulfate buffer containing 0.05M ammonium bicarbonate. This solution (3 ml) was loaded onto a Pharmacia Hi Load Phenyl Sepharose Pre-packed column and eluted by a wash of 90 ml of starting buffer followed by a batch elution with 210 ml of 0.05M ammonium bicarbonate. During this step of the separation, nicked hCG eluted along with a small quantity of non-nicked hCG of presumably a more hydrophilic form of non-nicked hCG than are the majority of non-nicked hCG molecules. Next, the major component of non-nicked hCG was eluted by applying 40% ethanol in 0.05M ammonium bicarbonate (90 ml).

Nicked hCG (preparation 813) was purified from parent CR 127 preparation by hydrophobic chromatography as described for non-nicked hCG.

Nicked hCG beta (preparation 834) was separated from CR 129 hCG beta by reverse phase chromatography in 0.1% TFA/acetonitrile buffer (Birken et al. 1991).

HCG beta core fragment (preparation 455) was prepared from Diosynth crude commercial hCG by modification of the method of Blithe (Blithe et al. 1988) gel filtration, Concanavalin A chromatography, and anion exchange, followed by reverse phase chromatography in 0.1% TFA/acetonitrile.

Other hormones: hLH (AFP-8270B), hLHβ (AFP-382) were kindly provided by the National Hormone and Pituitary Program, NIDDKD. HLHβcf were prepared as described by Birken (Birken et al. 1993).

Purification of Monoclonal Antibodies. Immunoglobulins were purified from ascites by the Protein A Monoclonal Antibody Purification System (Bio-Rad, Richmond, Calif.). The protein concentration of pure antibodies was determined by amino acid analysis. Purification of mABs was checked by a PAGE in the presence of SDS according to the method of Laemmli (Laemmli, 1953).

Iodination of Hormones And Monoclonal Antibodies. Antibodies and hormones were labeled with $^{125}$I by the chloramine T-method (Hunter and Greenwood, 1962).

Immunization of Mice And Cell Fusion. One group of Balb/c mice was immunized with nicked hCG (preparation 813), another was immunized with nicked hCGb (preparation 834) according the following protocol: the first immunization was carryed out subcutaneously with 15-20 µg of immunogen per animal in complete Freund's adjuvant; the second was carried but after two weeks with the same amount of intraperitoneally (ip) using 15 µg of antigen in PBS for each animal immune sera were tested for antibodies in liquid phase radio-immunoassay (RIA) using $^{125}$I-nicked hCGb. Mice with a high immune response were boosted with 15 µg hormone and after 3 days used for fusion.

Splenocytes from immunized mice were fused with cells of myeloma line X63-Ag8,653 (American Type Culture Collection) 3 days after the booster injection according to the method of Kohler and Milstein (Kohler and Milstein, 1975) as described in (Kovalevskaya et al. 1995). The splenocyte to myeloma cell ratio was 4:1 or 6:1. Polyethylene glycol 4000 (Sigma, St. Louis, Mo.) was used as the fusing reagent. On days 12-14 post fusion, culture supernatants (100 µl) from the wells with cell clones were screened for the presence of antibodies to hLHβcf using a liquid phase RIA. Positive selected cells were cloned at least two times by limiting dilutions on mouse peritoneal feeder cells. Subclones were injected ip into Balb/c mice (0.5×10$^6$ cells/mouse and mAB were purified from the ascites.

Isotypes of mABs were determined using ImmunoPure Monoclonal Antibody Isotyping Kit II (AP/PNPP) (Pierce, Rockford, Ill.) according to the manufacturer's instruction for the antigen-dependent technique.

Screening of Primary Clones and Immune Serum. Primary screening was carried out in a liquid phase RIA with 125I-nicked hCGb. The liquid phase RIA procedure has been described earlier (Birken et al., 1980). Briefly, the binding buffer consisted of PBS supplemented with 0.1% BSA and 0.1% sodium azide. 150 µl solution containing 30,000-40,000 cpm $^{125}$I-nicked hCGb was added to 100 Al culture supernatant diluted 25:1 with PBS. 50 µl of 8% normal mouse serum was also added. This solution was first incubated fro 1 hour at 37° C. and then overnight at 4° C. Following incubation, 500 µl of a 2.5% goat anti-mouse serum was added and mixture was incubated for 1 h at 37° C. followed by 2 hours at room temperature. The precipitate containing bound radioactive hormone was separated by centrifugation and counted in a gamma counter. Supernatants of positive clones were tested in the same type of assay to check cross-reactivity with $^{125}$I-hCG and $^{125}$I-hCGb. Immune serum was used as a positive control.

Competitive Liquid Phase RIA. Competitive liquid phase radioimmunoassays have been described previously (Kovalevskaya et al. 1995). Briefly they were conducted as follows: Cell supernatants were used at those dilutions at which approximately 40% of maximum antibody binding occurred in the absence of unlabeled hormones. The following regents were added to each 12×75 mm polystyrene tube: 100 µl diluted supernatant, 30,000-40,000 cpm of $^{125}$I-nicked hCG or $^{125}$I-nicked hCGb in 300 µl binding buffer (PBS), pH 7.2 with 0.1% BSA), 100 µl competitor solution and 100 µl 8% normal mouse serum. After incubation for 1 hour at 37° C. and overnight at 4° C., 1 ml of 2.5% goat anti-mouse serum was added as in the primary screening. Affinity constants were calculated by homologous competitive displacement assays using the PC version of the program Ligand by Munson (Munson and Rodbard, 1980).

Immunometric Assay For Nicked HCG. The methodology for the construction and validation of immunometric assays has been fully described (O'Connor et al., 1988). Briefly, the specificity of the antibody pairs and their capacity for simultaneous binding to antigen are determined as follows. The analytes tested for potential cross-reaction with the nicked hCG monoclonal antibodies included hCG, hCGβ, nhCGb, hCGβcf and hLH. The degree of cross reaction was anticipated from a knowledge of antibody specificity in liquid phase RIA.

The B151 antibody was absorbed onto the wells of microtiter plates (Immunlon IV, Dynatech, Chantilly, Va.) by incubating a 10 µg/ml solution in coating buffer (0.2 M bicarbonate, pH 9.5) overnight at 4° C. The coating antibody solution was aspirated, the plates washed (wash solution: 0.9% NaCl, 0.05% Tween 20) and blocked with a 1% solution of BSA in PBS with 0.1% sodium azide. Following incubation with the BSA solution (minimum 3 hours at room temperature) the blocking solution was removed, the wells again washed with wash solution and 200 µl/well of the appropriate nicked hCG standards or potential cross-reacting molecules were added in phosphate buffer B (0.05M phosphate with 0.1% bovine gamma globulin and 0.1% sodium azide) or in hCG-free serum (for serum assay) (Chemicon, TEMECULA Calif.) After overnight incubation 4° C., the plates were again aspirated and washed. The 200 µl (50,000 cpm-100,000 cpm) of B604 $^{125}$I-labeled antibody was added to the wells which were again incubated for 24 hours at 4° C. The tracer was aspirated, the plates washed with wash solution, the individual wells placed in glass tubes and the radioactivity determined in a Packard Cobra gamma counter. Doses were determined by interpolation from a smoothed spline transformation of the data points.

In addition to the nicked hCG assay, assay B109-B108* for intact hCG was employed. Prior to assay, the urines were thawed, the pH is adjusted with 1.0M Tris (pH 9.0), 50 µl/ml urine. The assay is performed from that point identically to that described for antibody characterization.

Recovery of Nicked HCG. Nicked hCG was assayed as described above using B151-B604* assay in the presence of increasing concentration of hCG (1.76-176 pmol/ml) with or without 10 g/ml B109 as a scavenger for hCG.

Subjects. Trophoblast serum and samples, Down syndrome samples and control normal pregnancy urine samples, ectopic pregnancy and spontaneous abortion samples were kind gift of Dr. L. Cole (Yale University). Matched serum/urine samples (5-6 weeks gestation age) obtained from practice CPMC physicians.

Creatinine. Creatinine determinations were performed in a 96-well microtiter plate format (Taussky, 1954).

Urine Processing. Twenty-four hour urine samples are collected from women undergoing embryo transfer as well as women in early natural pregnancy. The urine is refrigerated during the collection procedure. After delivery of the urine to the laboratory, sodium azide is added to 1 g/liter. Women undergoing in vitro embryo transfer are not pre-treated with hCG. Thus, all hCG which appears in their blood or urine is derived from the embryo (except for the small amounts of pituitary hCG present in all people). Raw urine is freed from particles by centrifugation followed by Pellicon filtration through a 0.45 micron membrane. Next, the procedure is to concentrate the urine with a Pellicon (Millipore) system which concentrates as much as 30 liters to 500 ml overnight (4° C.) using a 3,000 MW cutoff membrane. Smaller volumes can be concentrated in less that two hours. Next, the urine is desalted and delipidated by passage through a large volume of Sephadex G25 in 0.1 M ammonium bicarbonate. This step greatly increases the binding of CG to immunoaffinity columns. The desalted urinary concentrate is next size fractionated on the Pharmacia HiLoad Superdex 200 and the hCG and hCG subunit peaks are identified by specific immunoassays (O'Connor, J. F., et al., 1994) and the appropriate fractions are pooled and dried. The hCG and hCG subunits are purified from the gel filtered urine concentrate by immunoaffinity on insolubilized hCG antibody columns as described but with the use of either 4M guanadine (0.1M tris acetate, pH 5) or ammonium thiocyanate as eluant to decrease loss of sialic acid from the hormone. Alternatively, hCG is purified by conventional chromatographic procedures, anion exchange and hydrophobic chromatography. The subunits are separated on reverse phase HPLC using a 0.01M sodium phosphate, pH 5 buffer and acetonitrile, after incubation in 4M guanadine, 0.1M tris acetate, pH 5. A third method is final purification and separation of the hCG subunits on SDS PAGE electrophoresis followed by electroblotting to PVDF. The PVDF band can be subjected to protease digestion to release peptides and glycopeptides which can be separated on reverse phase HPLC in neutral pH 5 buffers.

Separation of Glycopeptides from Isolated hCG subunits. To facilitate isolation of the glycopeptides from the hCG subunits, the subunits are both tryptic digested and the products of digestion are separated on reverse phase HPLC (using a pH 5 buffer). This procedure results in removal of the large beta COOH-terminal peptide which contains O-linked sugars. It also releases small, non glycopeptides from both subunits (Pollak, S., et al., 1990, Birken, S., et al., 1987; Birken, S., et al., 1986). Next, the main disulfide-linked core of each hCG subunit, is reduced and carboxymethylated, and separated on reverse phase HPLC at pH 5. At this stage, large peptides are isolated, including the glycopeptides. Each separated glycopeptide is redigested with trypsin and re-separated on HPLC at pH 5. These glycopeptides are next employed for two different methods of sugar chain analysis. One method is the approach of releasing the oligosaccharides by enzymatic digestions uing PNGase F for the N-linked glycans. The released-glycans can be separated from the peptides by ethanol precipitation, desialyated with neuraminadase, and separated directly on a Dionex Carbopac PA-100 column. Oligosaccharide standards are available from Dionex, Oxford Glycosystems and other companies for calibrating column elution times for various glycans (Hardy, M. R., and Townsend, R. R., 1994, Rohrer, J. S., et al., 1993, Weitzhandler, M., et al., 1993; Townsend, R. R., et al., 1989). Confirmation of the released structures is obtained by performing carbohydrate compositional analysis of eluted glycan peaks as well as performing digestions with specific glycosidases and rechromatographing the modified glycan on the Dionex system (Hardy, M. R., and Townsend, R. R., 1994; Rohrer, J. S., et al 1993; Weitzhanlder, M., et al., 1993; Townsend, R. R., et al., 1989; Townsend, R. R., et al., 1991; Townsend, R. R., et al., 1989; Hardy, M. R., and Townsend, R. R., 1989; Townsend, R. R., et al., 1988; Hardy, M. R., et al, 1997; Hardy, M. R., and Townsend, R. R., 1988; Dionex, 1997; Spellman, M. W., 1990; Kumarasamy, R., 1990). The newly modified glycan can be observed to elute at the same time as the appropriate standard oligosacaharide and, in addition, the released monosaccharide can frequently be identified as well (Dionex, 1997). Structure determination is facilitated by the use of specific glycosidases for branch chain cleavage as well as for digestion of individual sugars from each of the branch chains. For example, Endo H cleaves high mannose type and hybrid oligosaccharide chains while glycosidase Endo F2 cleaves biantennary complex types and PNAase F cleaves tri and tetra-antennary chains down to the N-Asn bond.

Competitive receptor binding and in vitro bioassay. Bioassays are performed with recombinant-engineered CHO cells transfected with the human receptor to LH/CG Cells are maintained in Ham's F-12 medium, 4 mM Glutamine, 400 ug/ml G418 (Gibco), 5% fetal calf serum, 100 IU/ml penicillin, 100 ug/ml streptomycin. The cells are removed from the flask surface by versene only.

A competitive receptor assay constructed as follows: The receptor binding assay mixture contains 100 ul of the appropriate dilution of serum/urine samples or hCG dilutions for standard curve, 100 ul of $^{125}$-I-hCG (50,000-100,000 cpm) in buffer A(PBS/0.1% BSA) and 100 ul of CHO cells ($2\times10^5$ cells in PBS). The mixture is incubated at 37° C. with slight shaking followed by centrifugation for 10 minutes at 750×g. The supernatant is aspirated and the cell pellet is counted in gamma-counter.

In vitro bioassay. Transfected CHO cells are seeded (200,000 cells/well) into a 24 well plate in culture medium and incubated for 2-3 days until the cells reach confluence. Non-transfected CHO cells are included to monitor non-specific response. The medium is removed and replaced with medium containing 1 mM isobutylmethylxanthine with appropriate dilutions of tested serum or urine. The plates are incubated at 37° C. for two hours. The supernatant is removed, and the wells washed with Hank's balanced salt solution. The intracellular cAMP is extracted with 95% ethanol, which is diluted 1:5, (or up to 1:40, depending on cAMP content) in assay buffer provided by the cAMP kit (New England Nuclear). cAMP assay is performed according to manufacturer's instructions. Response is normalized to well protein content (BCA protein assay kit, Pierce, Rockford, Ill.).

In vivo bioassay is determined by the uterine weight assay in immature female mice, following the procedure of Wide and Hobson (Wide, L., and Hobson, B., 1987). The mice are injected subcutaneously with one third of the total dose of gonadotropin on three consecutive days and killed 72 hours after the first injection. Uteri are dissected free from mesentery, fat and oviducts, blotted to remove intrauterine fluid and weighed to the nearest 0.1 mg. Five to ten mice are used at each of these dose levels. The hCG standard preparation used is a nicked hCG. This material may be run concurrently with specimens isolated from first and third trimester pregnancy. Sham saline injection may be used as a control. The response signal is the log mouse uterine weight.

Clearance of hCG isoforms. The clearance of hCG is determined in the rat. Blood (200 ul/sample) is obtained at 0, 120, 240, 360 and 480 minutes post injection, from an indwelling catheter in an catheterized external jugular vein, following the procedure described by Newman et al. (Newman, C. B., et al., 1985) and Brown and Hedge (Brown, M. R., and Hedge, G. A., 1972). Briefly, adult male Sprague-Dawley rats (Charles River Laboratories, Wilmington Mass.), wt 175-225 g, are given free access to food and water. Rats are handled for acclimatization for one week after arrival, and several days before the hCG infusion, the rats are cannulated under pentobarbital anesthesia. A 21 gauge stainless steel cannula is inserted into the one external jugular vein. The placement of the catheter allows for the collection of blood from the unrestrained, unstressed rat. After the animals have recuperated from the cannula implacement, an hCG isoform is injected (10 μg/ml sterile saline) through the cannulated vein. Blood samples are obtained at the four time intervals listed above. The blood is allowed to clot and the serum separated and stored at −80° C. for immunometric assays specific for different hCG isoforms.

Clearance rate of the isoforms of hCG from the circulation of the rat are estimated by computer fitting the concentration data to an equation of the general form: Concentration=$Ae^{-\alpha t}$ +$Be^{-\beta t}$ at time t; A and α are parameters of the rapid component and B and β are parameters of the slow component. The metabolic clearance rate (MCR) is calculated as MCR=Dose/$(A/\alpha+B/\beta)$ and the initial volume of distribution is calculated from $V_d$=Dose/(A+B). The MCR is normalized to body weight for statistical analysis, which is performed using ANOVA with Duncan's range test for determination of significance (Cassals, J. W., et al., 1989).

Mice. The mouse species used in the experiments described herein are Balb/c mice, aged 12-20 weeks old and adult Sprague-Dawley rats of either sex. Mice used for the production of monoclonal antibodies through ascites and for the determination of in vivo biological activity as described. Balbc/c mice are used because hybridoma cell lines were developed using Balb/c splenocytes.

REFERENCES

Amano, J., R. Nishimura, S. Sato, and A. Kobata. 1990. *Glycobiology*. 1:45-50.

Armstrong, E. G., P. H. Ehrlich, S. Birken, J. P. Schlatterer, E. Siris, W. C. Hembree, and R. E. Canfield. 1984. *J. Clin. Endocrinol. Metab.* 59:867-874.

Baenziger, J. U. 1994. *FASEB J.* 8:1019-1025.

Bahl, O. P., L. Marz, and W. R. Moyle. 1995. pp. 125-44. In Anonymous In: Dufau M L, Means A R, ed. Hormone binding and target cell activation in the testis. New York, Plenum Press, 1974.

Birken, S., M. A. Kolks, S. Amr, B. Nisula, and D. Puett. 1987. *Endocrinology* 121:657-666.

Birken, S., Gawinowicz, M A, Kardana, A., Cole, L A. 1991. *Endocrinology* 129: 1551-1558.

Birken, S., Kovalevskaya, G., O'Connor, *J. Mol Cell Endocrinol,* 1996, 125:121-131.

Birken, S., M. A. Gawinowicz Kolks, S. Amr, B. Nisula, and D. Puett. 1986. *J. Biol. Chem.* 261:10719-10727.

Birken, S., Y. Chen, M. A. Gawinowicz, J. W. Lustbader, S. Pollak, G. Agosto, R. Buck, and J. O'Connor. 1993. *Endocrinology* 133:1390-1397.

Birken, S., Y. Maydelman, M. A. Gawinowicz, A. Pound, Y. Liu, and A. S. Hartree. 1996b. *Endocrinology* 137:1402-1411.

Blithe, D. L. and R. K. Iles. 1995. *Endocrinology* 136:903-910.

Braun, J. R., T. E. Willnow, S. Ishibashi, G. Ashwell, and J. Herz. 1996. *J. Biol. Chem.* 271:21160-21166.

Brown, M. R. and G. A. Hedge. 1972. *Neuroendocrinology.* 9:158-174.

Browne, E. S., M. V. Flasch, M. R. Sairam, and V. K. Bhalla. 1990. *Biochim. Biophys. Acta* 1033:226-234.

Cassals, J. W., Mann, K., Blithe, D. L., Nisula, B. C., Wehmann, R. E. 1989. *Cancer* 64:2313-2318.

Chang, P. L., Canfield, R. E., Ditkoff, E. C., O'Connor, J. F., Sauer, M. V., 1998. *Fertil. Steril.* 69:412-414.

Chmielewski, C. 1992. *ANNA. J.* 19:34-38.

Cole, L. A., A. Kardana, P. Andrade-Gordon, M. A. Gawinowicz, J. C. Morris, E. R. Bergert, J. O'Connor, and S. Birken. 1991a. *Endocrinology* 129:1559-1567.

Cole, L. A., A. Kardana, F. C. Ying, and S. Birken. 1991b. *Yale J. Biol. Med.* 64:627-637.

Cole, L. A., A. Kardana, S. Y. Park, and G. D. Braunstein. 1993. *J. Clin. Endocrinol. Metab.* 76:704-710.

Cole, L. A., S. Birken, and F. Perini. 1985. *Biochem. Biophys. Res. Commun.* 126:333-339.

Dionex. 1997. *Technical Note* 42

Elliott, M. M., A. Kardana, J. W. Lustbader, and L. A. Cole. 1997. *Endocrine* 7:15-32.

Ellish, N. J., Saboda, K, O'Connor, J, Nasca, P. C., Stanek, E F, Boyle, C. *Hum Reprod* 1996 11:406-412.

Fares, F. A., N. Suganuma, K. Nishimori, P. S. LaPolt, A. J. Hsueh, and I. Boime. 1992. *Proc. Natl. Acad. Sci. U.S.A.* 89:4304-4308.

Fiete, D., V. Srivastava, O. Hindsgaul, and J. U. Baenziger. 1991. *Cell* 67:1103-1110.

Grotjan, H. R. J. and L. A. Cole. 1989. In Microheterogeneity of Glycoprotein Hormones. H. R. J. Grotjan and L. A. Cole, editors. CRC Press, Boca Raton. 219-237.

Hakim, R. B., R. H. Gray, and H. Zacur. 1995. *Am. J. Obstet. Gynecol.* 172:1510-1517.

Hardy, M. R. and R. R. Townsend. 1988. *Proc. Natl. Acad. Sci. U.S.A.* 85:3289-3293.

Hardy, M. R., R. R. Townsend, and Y. C. Lee. 1997. *Anal Biochem* 1988 April;170(1):54-62, Hardy, M. R. and R. R. Townsend. 1989. *Carbohydr. Res.* 188:1-7.

Hardy, M. R. and R. R. Townsend. 1994. *Methods Enzymol.* 230:208-225.

Harrison, R. F. 1985. *Europ. J. Obstet. Gynec. reprod. Biol.* 20:159-168.

Hill, J. A. and D. J. Anderson. 1990. *Archsm. Immun. Ther. Exp.* 38:111-119.

Ho, H-H, O'Connor, J F, Overstreet, J W, Lasley, B L. 1997 *Early Pregnancy:Biology and Medicine,* 3:204-12.

Hoermann, R., G. Spoettl, M. Grossmann, B. Saller, and K. Mann. 1997. *J. Clin. Invest.* 71:953-960.

Hoermann, R., P. Berger, G. Spoettl, F. Gillesberger, A. Kardana, L. A. Cole, and K. Mann. 1994. *Clin. Chem.* 40:2306-2312.

Hussa, R. O. 1987. The Clinical Marker hCG. Praeger, New York.

Kagimoto, A., R. Sakakibara, N. Fukushima, N. Ikeda, and M. Ishiguro. 1995. *Biol. Pharm. Bull.* 18:810-817.

Kardana, A., G. D. Braunstein, and L. A. Cole. 1996. *Oncol. Res.* 8:13-16.

Kardana, A. and L. A. Cole. 1992. *Clin. Chem.* 38:26-33.

Karlsson, F. A., P. Burman, 0. Kampe, J. E. Westlin, and L. Wide. 1993. *Acta Endocrinol.* (Copenh) 129:291-295.

Kawasaki, T. and G. Ashwell. 1976. *J. Biol. Chem.* 251:1296-1302.

Kovalevskaya, G, Birken, S, O=Connor, J, Schlatterer, J, Maydelman, Y, Canfield, R. *Endocrine,* 1995, 3:881-887.

Kumarasamy, R. 1990. *J. Chromatogr.* 512:149-155.

Lasley, B. L., P. Lohstroh, A. Kuo, E. B. Gold, B. Eskenazi, S. J. Samuels, D. R. Stewart, and J. W. Overstreet. 1995. *Am. J. Ind. Med.* 28:771-781.

Maack, T., C. H. Park, and M. J. F. Camargo. 1985. In The kidney: Physiology and pathophysiology. D. W. Seldin and G. Giebisch, editors. Raven Press, New York. 1773-1803.

Matzuk, M. M., A. J. Hsueh, P. Lapolt, A. Tsafriri, J. L. Keene, and I. Boime. 1990. [published erratum appears in Endocrinology 1990 April;126 (4):2204]. *Endocrinology* 126:376-383.

Moyle, W. R., O. P. Bahl, and L. Marz. 1975. *Journal of Biological Chemistry* 250:9163-9169.

Newman, C. B., S. L. Wardlaw, and A. G. Frantz. 1985. *Life Sci.* 36:1661-1668.

Nishimura, R., T. Kitajima, K. Hasegawa, K. Takeuchi, and M. Mochizuki. 1989. *Jpn. J. Cancer Res.* 80:968-974.

Nishimura, R., T. Utsunomiya, K. Ide, T. Kitajima, H. C. Chen, J. L. Strobel, R. 0. Hussa, and M. Mochizuki. 1987. *Jpn. J. Cancer Res.* 78:833-839.

Nishimura, R., K. Ide, T. Utsunomiya, T. Kitajima, Y. Yuki, and M. Mochizuki. 1988. *Endocrinology* 123:420-425.

O'Connor, J., Kovalevskaya, G., Birken, S., Schlatterer, J. P., Schechter, D., McMahon, D., and Canfield, R. E. 1998. *Hum. Reprod.* 13:826-35.

O'Connor, J. F., S. Birken, J. W. Lustbader, A. Krichevsky, Y. Chen, and R. E. Canfield. 1994. *Endocr. Rev.* 15:650-683.

O'Connor, J. F., J. P. Schlatterer, S. Birken, A. Krichevsky, E. G. Armstrong, D. McMahon, and R. E. Canfield. 1988. *Cancer Res.* 48:1361-1366.

Odell, W. D. and J. Griffin. 1989. *J. Clin. Endocrinol. Metab.* 69:528-532.

Odell, W. D. and J. Griffin. 1987. *N. Engl. J. Med.* 317:1688-1691.

Pollak, S., S. Halpine, B. T. Chait, and S. Birken. 1990. *Endocrinology* 126:199-208.

Puisieux, A., D. Bellet, F. Troalen, A. Razafindratsita, C. Lhomme, C. Bohuon, and J. M. Bidart. 1990. *Endocrinology* 126:687-694.

Quadri, K. H., J. Bernardini, A. Greenberg, S. Laifer, A. Syed, and J. L. Holley. 1994. *Am. J. Kidney Dis.* 24:416-420.

Quenby, S. and R. G. Farquharson. 1994. *Fertil. Steril.* 62:708-710.

Ravindranath, N., N. S. Srilatha, M. R. Sairam, and N. R. Moudgal. 1992. *Indian J. Exp. Biol.* 30:982-986.

Rohrer, J. S., G. A. Cooper, and R. R. Townsend. 1993. *Anal. Biochem.* 212:7-16.

Sairam, M. R. and L. G. Jiang. 1992. *Mol. Cell Endocrinol.* 85:227-235.

Sairam, M. R. 1989. *FASEB J.* 3:1915-1926.

Sairam, M. R., J. Linggen, and G. N. Bhargavi. 1988. *Biosci. Rep.* 8:271-278.

Skarulis, M. C., R. E. Wehmann, B. C. Nisula, and D. L. Blithe. 1992. *J. Clin. Endocrinol. Metab.* 75:91-96.

Spellman, M. W. 1990. *Anal. Chem.* 62:1714-1722.

Stanton, P. G., G. Poznek, P. G. Burgon, D. M. Robertson, and M. T. W. Hearn. 1993. *J Endocrinol.* 138:529-543.

Szkudlinski, M. W., N. R. Thotakura, I. Bucci, L. R. Joshi, A. Tsai, J. East-Palmer, J. Shiloach, and B. D. Weintraub. 1993. *Endocrinology* 133:1490-1503.

Szkudlinski, M. W., N. R. Thotakura, J. E. Tropea, M. Grossmann, and B. D. Weintraub. 1995. *Endocrinology* 136:3325-3330.

Taussky, H. H. 1954. *J. Biol. Chem.* 208:853-861.

Thotakura, N. R., M. W. Szkudlinski, and B. D. Weintraub. 1994. *Glycobiology.* 4:525-533.

Townsend, R. R., M. Hardy, J. D. Olechno, and S. R. Carter. 1988. *Nature* 335:379-380.

Townsend, R. R., P. H. Atkinson, and R. B. Trimble. 1991. *Carbohydr. Res.* 215:211-217.

Townsend, R. R., M. R. Hardy, and Y. C. Lee. 1989. *Methods Enzymol.* 179:65-76.

Townsend, R. R., M. R. Hardy, D. A. Cumming, J. P. Carver, and B. Bendiak. 1989. *Anal. Biochem.* 182:1-8.

Weitzhandler, M., D. Kadlecek, N. Avdalovic, J. G. Forte, D. Chow, and R. R. Townsend. 1993. *J. Biol. Chem.* 268:5121-5130.

Wide, L. and B. Hobson. 1987. *Acta Endocrinol.* (Copenh) 116:465-472.

Wilcox, A. J., C. R. Weinberg, J. F. O'Connor, D. D. Baird, J. P. Schlatterer, R. E. Canfield, E. G. Armstrong, and B. C. Nisula. 1988. *N. Engl. J. Med.* 319:189-194.

Zinaman, M J, Clegg, E D, Brown, C C, O'Connor, J, Selevan, S G. *Fertil Steril.*, 1996, 65:503-509.

What is claimed is:

1. A diagnostic kit for determining the amount of an early pregnancy associated molecular isoform of hCG (EPMI-hCG) in a urine sample comprising:
   (a) a first antibody bound to a solid matrix, wherein the first antibody is B152, produced by the hybridoma deposited with the American Type Culture Collection under Designation No. HB-12467;
   (b) a second, labeled antibody which binds to the EPMI-hCG simultaneously with the first antibody, wherein the second antibody is B207, produced by the hybridoma deposited with the American Type Culture Collection under ATCC Designation No. PTA-1626; and
   (c) a control sample containing an amount of EPMI-hCG present in a urine sample of a normal pregnant subject.

2. A diagnostic kit for determining the amount of an early pregnancy associated molecular isoform of hCG (EPMI-hCG) in a urine sample comprising:
   (a) a first antibody bound to a solid matrix, wherein the first antibody is B152, produced by the hybridoma deposited with the American Type Culture Collection under Designation No. HB-12467;
   (b) a second, labeled antibody which binds to the EPMI-hCG simultaneously with the first antibody, wherein the second antibody is B207, produced by the hybridoma deposited with the American Type Culture Collection under ATCC Designation No. PTA-1626;
   (c) a third antibody bound to a solid matrix which binds to intact non-nicked hCG;
   (d) a fourth, labeled antibody which binds to intact non-nicked hCG simultaneously with the third antibody; and
   (e) a control sample containing an amount of EPMI-hCG present in a urine sample of a normal pregnant subject.

3. The diagnostic kit of claim 2, wherein the third antibody is B109 produced by the hybridoma deposited with the American Type Culture Collection under Designation No. PTA-1624.

4. The diagnostic kit of claim 2, wherein the fourth antibody is B108 produced by the hybridoma deposited with the American Type Culture Collection under Designation No. PTA-1625.

5. A diagnostic kit for determining the amount of an early pregnancy associated molecular isoform of hCG (EPMI-hCG) in a urine sample comprising:
   (a) B152 antibody produced by the hybridoma deposited with the American Type Culture Collection under Designation No. HB-12467; and
   (b) a second, labeled antibody which binds to EPMI-hCG simultaneously with the B152 antibody, wherein the second antibody is B207, produced by the hybridoma deposited with the American Type Culture Collection under ATCC Designation No. PTA-1626.

6. A diagnostic kit for determining the amount of an early pregnancy associated molecular isoform of hCG (EPMI-hCG) in a urine sample comprising:
   (a) B152 antibody produced by the hybridoma deposited with the American Type Culture Collection under Designation No. HB-12467;
   (b) a second, labeled antibody which binds to the EPMI-hCG simultaneously with the B152 antibody, wherein the second antibody is B207, produced by the hybridoma deposited with the American Type Culture Collection under ATCC Designation No. PTA-1626;
   (c) a third antibody bound to a solid matrix which binds to intact non-nicked hCG; and
   (d) a fourth, labeled antibody which binds to intact non-nicked hCG simultaneously with the third antibody.

* * * * *